United States Patent
Shores et al.

(10) Patent No.: US 9,636,072 B2
(45) Date of Patent: May 2, 2017

(54) COMPUTED TOMOGRAPHY BREAST IMAGING AND BIOPSY SYSTEM

(71) Applicant: Fischer Medical Technologies, LLC, Broomfield, CO (US)

(72) Inventors: Ronald B. Shores, Greenwood Village, CO (US); Morgan Nields, Englewood, CO (US); David E. Gustafson, Westminster, CO (US); Michael Tesic, Superior, CO (US)

(73) Assignee: FISCHER IMAGING, INC., Cumming, GA (US)

( * ) Notice: Subject to any disclaimer, the term of this patent is extended or adjusted under 35 U.S.C. 154(b) by 495 days.

(21) Appl. No.: 14/012,547

(22) Filed: Aug. 28, 2013

(65) Prior Publication Data

US 2014/0037048 A1 Feb. 6, 2014

Related U.S. Application Data

(63) Continuation of application No. 12/197,939, filed on Aug. 25, 2008, now abandoned.

(Continued)

(51) Int. Cl.
 *A61B 19/00* (2006.01)
 *A61B 6/00* (2006.01)
 (Continued)

(52) U.S. Cl.
 CPC .............. *A61B 6/502* (2013.01); *A61B 6/032* (2013.01); *A61B 6/0435* (2013.01);
 (Continued)

(58) Field of Classification Search
 CPC ......... A61B 6/032; A61B 6/0435; A61B 6/06; A61B 6/4085; A61B 6/466; A61B 6/502; A61B 6/04
 See application file for complete search history.

(56) References Cited

U.S. PATENT DOCUMENTS 5,078,142 A 1/1992 Siczek et al.
5,240,011 A 8/1993 Assa
(Continued)

FOREIGN PATENT DOCUMENTS

EP 1700568 A2 9/2006
WO 2006119426 A2 11/2006
WO WO 2007/095312 8/2007

OTHER PUBLICATIONS

Richard A. Sones et al., "A Detector for Scanned Projection Radiography", Radiology, vol. 175, pp. 553-559, 1990.
(Continued)

*Primary Examiner* — Katherine Fernandez
*Assistant Examiner* — Helene Bor
(74) *Attorney, Agent, or Firm* — Matthew L. Grell; Jeffrey C. Watson; Grell & Watson Patent Attorneys

(57) ABSTRACT

A prone CT breast x-ray imaging system is described that can image a full breast to create a conventional two-dimensional digital image in very high resolution (e.g., ≤25 micron pixels). The system is capable of imaging the entire breast in three-dimensional based on multiple projection views from a one-dimensional or two-dimensional detector. Data can be acquired and reconstructed with a limited number of views from limited angles or with conventional cone beam CT algorithms. The resulting three-dimensional image enables the detection and diagnosis of fine micro calcifications and small masses as may be distributed throughout the breast, thus allowing radiologists to make an improved determination of malignancy as opposed to conventional two-dimensional digital mammography. In addition, the injection of intravenous contrast in conjunction with or without pre and post contrast subtraction imaging provides a radiologist with morphologic information on the existing tumor burden in the breast. This capability may obviate the need for an independent contrast MRI exam of the breast which is increasingly performed for local staging and determination of tumor extent in a patient with a known cancer. Integrated biopsy capability permits convenient and rapid biopsy of any area suspicious for malignancy.

17 Claims, 11 Drawing Sheets

Related U.S. Application Data

(60) Provisional application No. 61/034,336, filed on Mar. 6, 2008, provisional application No. 60/957,620, filed on Aug. 23, 2007.

(51) Int. Cl.
*A61B 6/03* (2006.01)
*A61B 6/04* (2006.01)
*A61B 90/00* (2016.01)

(52) U.S. Cl.
CPC ............ *A61B 6/4452* (2013.01); *A61B 6/466* (2013.01); *A61B 6/4021* (2013.01); *A61B 6/482* (2013.01); *A61B 2090/364* (2016.02)

(56) References Cited

U.S. PATENT DOCUMENTS

| | | | |
|---|---|---|---|
| 5,278,416 A * | 1/1994 | Pierfitte | A61B 6/4441 250/363.05 |
| 5,289,520 A | 2/1994 | Pellegrino et al. | |
| 5,386,447 A | 1/1995 | Siczek | |
| 5,409,497 A | 4/1995 | Siczek et al. | |
| 5,415,169 A | 5/1995 | Siczek et al. | |
| 5,514,874 A | 5/1996 | Boone et al. | |
| 5,526,394 A | 6/1996 | Siczek et al. | |
| 5,569,266 A | 10/1996 | Siczek | |
| 5,712,483 A | 1/1998 | Boone et al. | |
| 5,735,264 A | 4/1998 | Siczek et al. | |
| 5,803,912 A | 9/1998 | Siczek et al. | |
| 5,917,881 A | 6/1999 | Jeffery | |
| 5,999,587 A | 12/1999 | Ning et al. | |
| 6,022,325 A * | 2/2000 | Siczek | A61B 6/0435 348/E13.014 |
| 6,052,427 A | 4/2000 | Pan | |
| 6,075,836 A | 6/2000 | Ning | |
| 6,102,866 A | 8/2000 | Nields et al. | |
| 6,272,200 B1 | 8/2001 | Pan et al. | |
| 6,298,110 B1 | 10/2001 | Ning | |
| 6,324,242 B1 | 11/2001 | Pan | |
| 6,459,925 B1 | 10/2002 | Nields et al. | |
| 6,463,122 B1 * | 10/2002 | Moore | A61B 6/0435 378/17 |
| 6,477,221 B1 | 11/2002 | Ning | |
| 6,480,565 B1 | 11/2002 | Ning | |
| 6,504,892 B1 | 1/2003 | Ning | |
| 6,528,793 B1 | 3/2003 | Chen et al. | |
| 6,618,466 B1 | 9/2003 | Ning | |
| 6,678,546 B2 | 1/2004 | Toker et al. | |
| 6,846,289 B2 | 1/2005 | Besson et al. | |
| 6,891,920 B1 | 5/2005 | Minyard et al. | |
| 6,987,831 B2 | 1/2006 | Ning | |
| 7,092,482 B2 | 8/2006 | Besson | |
| 7,099,428 B2 | 8/2006 | Clinthorne et al. | |
| 7,227,924 B2 | 6/2007 | Zhou et al. | |
| 7,245,692 B2 | 7/2007 | Lu et al. | |
| 7,245,755 B1 | 7/2007 | Pan et al. | |
| 7,319,734 B2 | 1/2008 | Besson et al. | |
| 7,352,887 B2 | 4/2008 | Besson | |
| 7,362,845 B2 | 4/2008 | Ning | |
| 7,394,889 B2 | 7/2008 | Partain et al. | |
| 7,406,150 B2 | 7/2008 | Minyard et al. | |
| 7,831,015 B2 | 11/2010 | Li et al. | |
| 2001/0005410 A1 * | 6/2001 | Rasche | A61B 6/4441 378/197 |
| 2004/0202360 A1 | 10/2004 | Besson | |
| 2005/0129172 A1 | 6/2005 | Mertelmeier | |
| 2005/0249432 A1 | 11/2005 | Zou et al. | |
| 2006/0094950 A1 | 5/2006 | Ning | |
| 2006/0262898 A1 | 11/2006 | Partain et al. | |
| 2007/0036418 A1 | 2/2007 | Pan et al. | |
| 2007/0104313 A1 * | 5/2007 | Tesic | A61B 5/1075 378/37 |
| 2007/0253528 A1 | 11/2007 | Ning et al. | |
| 2007/0274435 A1 | 11/2007 | Ning et al. | |
| 2007/0280408 A1 | 12/2007 | Zhang | |
| 2008/0089468 A1 * | 4/2008 | Heigl | A61B 6/032 378/20 |
| 2008/0187095 A1 | 8/2008 | Boone et al. | |
| 2008/0226018 A1 | 9/2008 | Partain et al. | |
| 2008/0226036 A1 * | 9/2008 | Timmermans | A61B 6/4464 378/198 |
| 2008/0292055 A1 | 11/2008 | Boone | |
| 2009/0087045 A1 | 4/2009 | Partain et al. | |

OTHER PUBLICATIONS

Mike M. Tesic, et al., "Digital Radiography of the Chest: Design Features and Considerations for a Prototype Unit", Radiology, vol. 148, No. 1, pp. 259-264, Jul. 1983.

R.A. Mattson, et al., "Design and Physical Characteristics of a Digital Chest Unit", SPIE, Digital Radiography, vol. 314, 6 pages, 1981.

John J. Gisvold, et al., "Computed Tomographic Mammography (CTM)" AJR, vol. 33, pp. 1143-1149, Dec. 1979.

John Boone et al., "Computed Tomography for Imaging the Breast", Journal Mammary Gland Biol Neoplasia (2006) 11: 103-111, Apr. 2006, 9 pages.

Lehman CD et al., "Cancer Yield of Mammography, MR and U.s. in High-Risk women: Prospective Multi-Institution breast Cancer Screening Study", Radiology vol. 244: No. 2, Aug. 2007, 10 pages.

Kreige M. et al., "Efficacy of MRI and Mammography for Breast-Cancer Screening in Women with a Familiar or Genetic Predisposition", The New England Journal of Medicine, vol. 351 No. 5, Jul. 29, 2004, 11 pages.

Leach M. et al., "MRI Surveillance for Hereditary Breast-Cancer Risk", The Lancet, vol. 365, May 21, 2005, 3 pages.

Salslow D. et al., "American Cancer Society Guidelines for Breast Screening with MRI as an Adjunction to Mammography", CA A Cancer Journal for Clinicians, vol. 57, No. 2, Mar./Apr. 2007, 17 pages.

Lehman, "MRI Evaluation of the Contralateral Breast in Women with Recently Diagnosed Breast Cancer", The New England Journal of Medicine, vol. 356, No. 13, Mar. 29, 2007, 9 pages.

Pediconi F., "Contrast-Enhanced MR Mammography for Evaluation of the Contralateral Breast in Patients with Diagnosed Unilateral Breast Cancer of High-Risk Lesions", Radiology, vol. 243: No. 3, Jun. 2007, 13 pages.

Inoue et al., "Dynamic Multidetector CT of Breast Tumors: Diagnostic Features and Comparison with Conventional Techniques", American Journal of Roentgenology, AJR: 181, Sep. 2003, 8 pages.

Tozaki et al., "Diagnosis of Tis/T1 Breast Cancer Extent by Multislice Helical CT: A Novel Classification of Tumor Distribution", Radiation Medicine, vol. 21, No. 5, 2003, 6 pages.

C.H. Joseph Change, et al., Computed Tomographic Evaluation of the Breast, American Roentgen Ray Society, Feb. 28, 1978, 6 pages.

Li, Yuying and Santosa, Fadil, "A Computational Algorithm for Minimizing Total Variation in Image Restoration", IEEE Transactions on Image Processing, vol. XX, No. Y, 1996.

Peng, Hui and Stark, Henry, "Image Recovery in Computer Tomography from Partial Fan-Beam Data by Convex Projections", IEEE Transactions on Medical Imaging, Vo. 11, No. 4, pp. 470-478, Dec. 1992.

Emmanuel Candes et al., "Signal Recovery from Random Projections", Computational Imaging III, Proceedings of SPIE-IS&T Electronic Imaging, SPIE vol. 5674, pp. 76-86, Mar. 2005.

* cited by examiner

COMPUTED TOMOGRAPHY BREAST IMAGING AND BIOPSY SYSTEM

RELATED APPLICATIONS

This application is a continuation of U.S. patent application Ser. No. 12/197,939, filed Aug. 25, 2008, entitled "COMPUTED TOMOGRAPHY BREAST IMAGING AND BIOPSY SYSTEM," which claims the benefit of U.S. Provisional Application No. 60/957,620, filed Aug. 23, 2007, entitled "PRONE BREAST IMAGING AND BIOPSY SYSTEM," and U.S. Provisional Application No. 61/034,336, filed Mar. 6, 2008, entitled "TOMOGRAPHY BREAST IMAGING AND BIOPSY SYSTEM," the entirety of each of which is hereby incorporated by reference.

FIELD OF THE INVENTION

The present invention relates to medical imaging and biopsy systems and methods, and in particular, to improved systems and methods that may be particularly apt for prone breast imaging and biopsy, including imaging with divergent beams (e.g., fan beams and cone beams), computed tomography (CT) processing and/or slot scan image signal detectors.

BACKGROUND

Existing prone breast biopsy systems such as described in U.S. Pat. No. 5,078,142 to Siczek et al. and U.S. Pat. No. 5,289,520 to Pellegrino et al. allow stereotactic needle biopsy of a breast, but with a limited field of view, e.g., typically a field of view of only 5 cm×5 cm. In cases where poorly visualized microcalcifications are detected on a screening mammogram, or as a result of diagnostic mammography, it is difficult to position that portion of the breast in the small field of view provided by the prone biopsy system, given the subtle nature of the microcalcifications and the lack of well defined landmarks in the breast. In addition, microcalcifications frequently involve one or more quadrants of the breast and sampling tissue from several areas is challenging for the radiologist and extends procedure time as the breast needs to be constantly repositioned and recompressed for additional imaging and biopsy.

Mammography and ultrasound are commonly employed to determine the extent of cancer present in a patient's breast once a known tumor has been diagnosed by ultrasound or stereotactic x-ray needle biopsy. However the sensitivity of mammography and ultrasound together falls short of the sensitivity provided by magnetic resonance imaging (MRI) with contrast.

Contrast MRI is extremely sensitive to the presence of breast cancer (>95% sensitivity), although MRI specificity is reported significantly lower at 30% to 60%. MRI imaging exams of one or both breasts are increasingly requested by radiologists and surgeons for patients with a known breast cancer, in order to determine the extent of disease. Should multifocality be detected (i.e., cancer present in more than one area of the breast) or if cancer is detected in the contralateral breast, surgical treatment may be more extensive, up to and including bilateral mastectomy. On the other hand, should no additional disease be detected by the MRI exam, a minimal surgical procedure such as a lumpectomy may be the preferred form of treatment. In addition to determining local extent of breast cancer ("local staging") MRI breast imaging can also be employed to search for small cancers in asymptomatic women where cancer may be expected to develop.

In relation to the foregoing, several multi-institutional studies have now shown that MRI is an effective method of screening women who are at risk for breast cancer. See, e.g., Lehman CD et al., "*Cancer Yield of Mammography, MR and U.S. in High-Risk Women: Prospective Multi-Institution Breast Cancer Screening Study,*" Radiology, (August 2007); Kreige M. et al., "*Efficacy of MRI and Mammography for Breast-Cancer Screening in Women with a Familiar or Genetic Predisposition,*" New England Journal of Medicine, (Jul. 29, 2004); and Leach M. et al., "*MRI Surveillance for Hereditary Breast Cancer Risk,*" The Lancet, Volume 365 at 1769-1778 (2005). The American Cancer Society has recently adopted guidelines for annual MRI breast screening for women who have a lifetime risk of 20-25%. See, e.g., Saslow D. et al., "*American Cancer Society Guidelines for Breast Screening with MRI as an Adjunction to Mammography,*" CAA Cancer Journal for Clinicians, Volume 57 at 75-89 (2007). As many as 1.2 million women could be considered at high risk for breast cancer based on the guidelines, suggesting a need for significant MRI capacity for annual breast cancer screening.

In addition to screening for breast cancer with MRI, and as noted above, a role has emerged for MRI imaging of the contralateral breast when a breast cancer is diagnosed. Several studies have shown an incidence ranging from 3 to 18%. See, e.g., Lehman, "*MRI Evaluation of the Contralateral Breast in Women with Recently Diagnosed Breast Cancer,*" New England Journal of Medicine, Volume 356 at 1295-1303 (2007); Pediconi F., "*Contrast-Enhanced MR Mammography for Evaluation of the Contralateral Breast in Patients with Diagnosed Unilateral Breast Cancer or High-Risk Lesions,*" Radiology, Volume 243: Number 3 (June 2007). About 250,000 breast cancers are found annually in the United States (invasive and DCIS) suggesting that a cost effective procedure to rule out cancer in the contralateral breast will likely become a standard of care.

A significant limitation with MRI imaging of the breast is the difficulty of acquiring tissue using needle biopsy techniques. In this regard, an MRI guided breast biopsy is more difficult and time consuming than an ultrasound or stereotactic x-ray guided needle biopsy due to instrument requirements, and limited breast access.

That is, in MRI procedures the patient is normally positioned in the bore of a magnetic resonance MR scanner in a strong magnetic field that requires special non-metallic biopsy instruments capable of functioning within a strong magnetic field. In addition, since MRI patients are imaged in a prone position with the breast hanging pendulant within a breast coil, access to the medial portion of the breast is difficult as is access to tissue near the chest wall since most needle biopsy solutions for MRI systems provide only a lateral approach with a Cartesian grid location system, which by design necessarily inhibits needle access to tissue adjacent to the chest wall.

In addition to the foregoing, since the specificity of MRI in breast imaging is not as high as the sensitivity, it is difficult for many radiologists to confidently interpret an enhancing lesion of the breast with MRI without the performance of a difficult and time consuming needle biopsy procedure. As such, some physicians prefer not to order an MRI exam unless biopsy of all enhancing areas can be undertaken in order to provide the patient assurance that these areas of enhancement were indeed benign. In turn, MRI enhancement in a patient known to have breast cancer can create more uncertainty than if the exam had not been performed.

Finally, MRI imaging is also expensive compared to ultrasound or mammography and the procedure is not normally available in a breast center for near immediate scheduling such as other breast imaging procedures. For the noted reasons, alternatives to MRI breast imaging are of high interest.

Some imaging centers have experimented with contrast injection in conjunction with conventional multi detector CT (MDCT) imaging. The published results appear to be very similar to MRI imaging of the breast with contrast. See, e.g., Inoue et al., "*Dynamic Multidetector CT of Breast Tumors: Diagnostic Features and Comparison with Conventional Techniques,*" American Journal of Roentgenology, (September 2003); Tozaki et al., "*Diagnosis of Tis/T1 Breast Cancer Extent by Muftislice Helical CT: A Novel Classification of Tumor Distribution,*" Radiation Medicine, Volume 21: No. 5, at 187-192, (2003). However, conventional CT breast imaging techniques subject patients to radiation levels that are higher than desired due to the classical design of the axial CT scanner which necessarily images the entire thorax (i.e., lungs and heart) in order to include the breasts in the imaging field. In addition, state of the art conventional multidetector CT scanners (MDCT) are limited to providing spatial resolution of about 1 lp/mm. Further, this resolution may be achieved only with high resolution kernels (e.g., bone kernel) at the expense of increased image noise.

The ability to diagnose breast cancer based on morphologic imaging depends both on the uptake of contrast material into the cancerous tissue as well as the spatial frequency of the image, since breast cancer is frequently indicated by thin straight lines (i.e., spiculation) emanating from a lesion. Benign masses such as fibroadenomas are normally characterized by smooth oval shapes which may also take up contrast. MRI imaging of the breast allows a three-dimensional review of the entire breast with capabilities such as MIP (maximum intensity projection) and with MR pulse sequences which suppress signals from fat (fat suppression imaging) to improve the conspicuity of the contrast in the tumor and parenchymal tissue.

Prototype prone breast x-ray imaging systems that use cone beam CT in conjunction with commercially available flat panel digital detectors have been described. See, e.g., U.S. Pat. No. 6,987,831 B2 to Ning; and John Boone et al., "Computed Tomography for Imaging the Breast," Journal Mammary Gland Biol Neoplasia, 11(2) at 103-111, (April, 2006). These systems acquire a series of cone beam views as the flat panel and x-ray source rotate around the breast and the images are reconstructed into three-dimensional images using cone beam CT algorithms. The flat panels provide an intrinsic pixed size of about 100-200 microns or spatial resolution of 2.5-5 lp/mm. X-ray scatter provides design challenges as each view is essentially a digital mammogram of the entire uncompressed breast and using conventional static or moving grids to reduce scatter increases image processing complexities. In addition, the kilovoltage as described for these systems ranges up to 80 kVp which will produce images of lower contrast than conventional digital mammography systems which typically use kilovoltage in the range of 30-40 kVp.

SUMMARY

In one aspect of the present invention, a breast imaging apparatus is provided that includes a locator for positioning a patient's breast within a predetermined frame of reference having a predetermined axis extending away from a boundary plane of the predetermined frame of reference, wherein an axis of a patient's breast that extends from a patient's chest wall through a patient's breast nipple may be aligned with the predetermined axis for imaging. In this regard, the apparatus may further include an imaging source beam (e.g., an x-ray beam source) for transmitting an imaging beam through the predetermined frame of reference, and an imaging beam detector for receiving the imaging beam and providing an output signal in response thereto.

One or both of the imaging beam source and imaging detector may be moveable relative to the predetermined frame of reference, wherein the apparatus is operable to provide an output signal that comprises projection image data corresponding with a predetermined angular range of different projection views of a patient's breast. In turn, the apparatus may include a processor for processing the projection image data to provide a reconstructed image. For example, in one approach computed tomography processing may be employed to yield one or more reconstructed three-dimensional image(s). In this regard, computed tomography may preferably refer to image reconstruction approaches (e.g., software algorithms) that process image data corresponding with a predetermined number of projection views (e.g., at least 10 projections) obtained across a predetermined angular range (e.g., more than 50°) relative to a patient breast axis. The reconstructed image(s) may be advantageously displayed on a user display.

In another aspect, image data corresponding with a given view of a patient's breast may be utilized (e.g., by a processor) to generate quasi real-time images, e.g., fluoroscopic images, wherein the quasi real-time images may be displayed on a quasi real-time basis, thereby facilitating biopsy, surgical and/or treatment procedures. In this regard, stereotactic imaging or computed tomography imaging may be employed in a first mode of operation that yields one or more images for review by medical personnel. Then, in a second mode of operation fluoroscopic imaging may be employed to generate quasi real-time images that may be displayed and reviewed by medical personnel in conjunction with the positioning of biopsy, surgical and/or treatment devices.

By way of primary example, the locator for positioning the patient's breast may include a table for supporting the patient in a prone position, wherein the table includes at least one aperture for receiving a patient's pendulant breast therethrough, wherein the breast extends into a predetermined frame of reference for imaging that is defined below the table. Relatedly, the table may be provided for selective, vertical positioning, thereby providing enhanced access to and positioning of a patient's breast within the imaging predetermined frame of reference.

In some applications, a breast positioning device may be provided. For example, in one approach, a cup-shaped member may be supportably interconnected to the apparatus and selectively positionable to maintain a patient's breast in a given position, (e.g., in a position in which the breast axis is aligned with the predetermined axis of the predetermined frame of reference) below a patient support table. In this regard, the cup-shaped member may be sized to maintain the position of a breast, while avoiding the application of compressive forces thereto. In certain embodiments the cup-shaped member may comprise one or more aperture(s) or cut-out portion(s) to facilitate the passage of biopsy, surgical and/or treatment devices therethrough. In other embodiments, opposing compression plates may be provided for breast positioning.

A unique feature of embodiments of the present invention is to allow the imaging and biopsy of very small, difficult to visualize microcalcifications. In one approach, a slot scan imaging detector with imaging capability of 25 microns or smaller may be positioned behind the area of interest (e.g., a region of a patient's breast located within a predetermined frame of reference) and may scan in order to produce a high resolution image of the calcifications. High spatial resolution of microcalcifications may provide further diagnostic information to the radiologist regarding the potential for malignancy.

Should the radiologist determine that tissue biopsy, surgical removal and/or treatment is required the slot scan detector may scan in a reciprocating fashion to provide a quasi real time (<30 fps) fluoroscopic image of the calcifications enabling tissue biopsy under image guidance. For example, as a biopsy needle is positioned into an area to be biopsied the fluoroscopic image may provide an ability to dynamically direct the needle into the area of interest and to confirm the position of the needle relative to the calcifications to be biopsied. Images acquired at a higher dose, e.g., similar to a "snapshot" image can be taken and archived so that there is a medical record of exactly where the biopsy needle was positioned. In addition, the slot scan detector provides increased primary to scatter x-ray ratio yielding improved contrast resolution to allow better delineation of the extent of disease for mass lesions.

In certain embodiments, the imaging beam source and imaging detector may be positioned and the processor may be configured to create a stereotactic pair of images or a CT image of the breast, wherein one or more two-dimensional and/or three-dimensional breast image(s) may be reconstructed or generated from multiple projection views. Stereo imaging can be performed with or without compression. In turn, the imaging beam source and imaging detector may be positioned and the processor may be further configured for fluoroscopic imaging, thereby facilitating the real-time display of images that show the progressive positioning of biopsy, surgical and/or treatment devices. Further, a needle biopsy assembly may be employed that has software that is able to calculate the appropriate trajectory for a needle to be positioned in the area of interest in order to carry out a needle biopsy procedure as is currently practiced in needle biopsy of the breast. By way of example, biopsy-related technology may be employed as described in U.S. Pat. No. 5,735,264 issued to Siczek et al., and U.S. Pat. No. 6,022,325 issued to Siczek et al., the entirety of each of which is hereby incorporated by reference.

The utilization of a slot scan detector in various embodiments may reduce x-ray scatter, improve the operative signal to noise ratio, reduce x-ray dosage, and in an embodiment, may produce a line of image data approximately every 200-300 microseconds using time delay and integration, as described in U.S. Pat. No. 5,526,394 to Siczek et al., the entirety of which is hereby incorporated by reference.

As employed herein a "slot scan imaging detector" refers to a detector having an array of detector elements, wherein during imaging operations an active array of the elements (e.g., elements from which accumulated charge is shifted to yield an output signal comprising image data) may be scanned across a region of interest of a patient's breast in a direction substantially parallel to the patient's chest wall. In this regard, a length of the active array may be oriented substantially orthogonal to a patient's chest wall (e.g., parallel to a center axis of a predetermined frame of reference for imaging the patient's breast), and a width of the active array may be less than a width of the imaged region of interest (e.g., a width of a patient's breast).

In one implementation, a slot scan imaging detector may be provided to define an active array comprising a plurality of detector elements aligned in a single column. In another implementation, an imaging detector may be provided to define an active array comprising a plurality of detector elements arranged in a plurality of parallel columns and corresponding rows, wherein accumulated charge resulting from the receipt of an imaging beam may be shifted along a row of detector elements (e.g., from column to column) to operate in a time delay and integration mode.

In one approach, an active array of detector elements may be mechanically scanned (e.g., physically moved) in relation to a patient's breast within a predetermined frame of reference during slot scanning operations. In another approach, a detector array may be utilized that is of a size sufficient to remain stationary (e.g., the array may be of a length and width that is greater then the length and width of a patient's breast to imaged), wherein a dynamically changing, active array of such detector elements may be electrically scanned during slot scan operations by successively shifting out charge from a different element column or different adjacent sets of detector element columns across the detector array during each successive time interval. In each of the noted approaches, an imaging signal may be scanned across a patient's breast in timed relation to detector scanning operations. For example, in one embodiment a narrow beam, e.g., a fan beam, may be scanned across a patient's breast in synchronous relation to active detector array scanning, wherein the beam and active array are maintained in aligned relation during imaging.

In various embodiments of the present invention, the imaging beam source or multiple imaging beam sources and/or the imaging signal detector may be separately positionable relative to the predetermined framed of reference. In this regard, in certain implementations, an imaging beam source and/or imaging signal detector may be independently positionable to yield a plurality of different projection views.

More particularly, in some embodiments a moveable first member may be provided to support the imaging beam source, wherein an imaging beam source is selectively positionable across a first predetermined angular range relative to the predetermined axis of the predetermined frame of reference. For example, the first support member may be pivotable about the predetermined axis of the predetermined frame of reference, wherein the imaging beam source may be selectively, radially positioned across the first predetermined angular range.

Similarly, a moveable, second support member may be provided for supporting the imaging signal detector. In one approach, the second support member may be pivotable about the predetermined axis of the predetermined frame of reference, wherein the imaging signal detector may be selectively, radially positioned across a second predetermined angular range relative to the predetermined axis.

As may be appreciated, the separate moveability of the imaging beam source and imaging signal detector yields an arrangement in which multiple projection views may be readily obtained in a wide variety of approaches. Further, such an arrangement facilitates access to a patient's breast by medical personnel. For example, in certain implementations, 360° access to a patient's breast may be realized. Such access may be of particular advantage in relation to breast biopsy, surgical and/or treatment procedures carried out during and with the visual assistance of CT image generation.

Additional image reconstruction capability may be enhanced by the use of new algorithms where a limited number of views, and limited angles, can be utilized to reconstruct image data thus delivering a reduced dose of x-ray to the patient. By way of example, image reconstruction may employ approaches disclosed in PCT Publication No. WO2007/095312, published Aug. 23, 2007, corresponding with PCT Application No. PCT/US2007/003956 entitled "IMAGE RECONSTRUCTION FROM LIMITED OR INCOMPLETE DATA," the entirety of which is hereby incorporated by reference.

Embodiments of dedicated prone breast CT imaging systems may image a complete breast with an absorbed radiation level similar to that of bi-lateral mammography. In an embodiment, a dedicated cone beam, slot scanning imaging system with a high-resolution detector may provide a spatial resolution of about 10-15 lp/mm. Embodiments of systems described herein may include the use of contrast media, wherein a three-dimensional reconstruction using cone beam CT as described herein may allow similar review capabilities, as compared to MRI, when the precontrast image (may be) registered and subtracted from the post contrast image. Additionally, as described in Seo et al., *Journal of Clinical Imaging*, 29, at 172-178 (2005), the increase in Hounsfield Unit (HU) density of the area of contrast uptake may allow visualization of tumor enhancement without subtraction even at low dose. Such a reconstruction may have significantly higher spatial resolution than an MRI image or conventional Multi-Detector Computed Tomography (MDCT) image. Voxel linear dimensions on the order of 0.8 mm to 1.00 mm are available with MRI or MDCT systems while a dedicated cone beam CT system as described herein will permit voxel sizes on the order of 100 microns or smaller for small areas of interest where higher resolution may be required. For example, a detector pixel size of 25 microns may allow a three-dimensional image to be reconstructed at a voxel linear dimension smaller than 25 microns depending on the geometry of the imaging system.

Embodiments of systems described herein may be similar in layout to the stereotactic biopsy tables of prior art products. Embodiments of systems described herein may provide an imaging detector that may extend from the anterior portion of the breast to the chest wall and an x-ray field that may be collimated to the length and width of a one-dimensional or two-dimensional detector. This system may be capable of creating a three-dimensional cross sectional x-ray image of the breast while avoiding ionizing radiation to the lungs and heart. This type of dedicated breast CT imaging system may be able to demonstrate the extent of cancer in the breast following the intravenous injection of non-ionic contrast similar to the MRI breast imaging exam. The lower cost of this type of imaging system compared to the cost of an MRI imaging system and per procedure cost may provide improved access to patients for an important exam that could help the patient and surgeon determine an optimal course of surgical treatment. The lower cost may also allow screening of women at high risk for breast cancer in place of the more expensive MRI exam. The breast CT imaging system described herein is capable of producing a CT image of the breast at a radiation dose level equal to or less than two-view mammography while the non-ionic contrast used in the CT imaging procedure has an improved safety profile over gadolinium agents used with MRI exams.

In addition, a cone beam CT imaging system described herein may be compatible with known biopsy or ablation systems that may be used for biopsy or treatment of identified tissue targets. In contrast, it has been difficult to develop biopsy or ablation technologies (RF, microwave, High Intensity Focused Ultrasound (HIFU), etc.) that are compatible with MRI systems due to the presence of strong magnetic fields and RF and gradient coil subsystems.

An added benefit of a cone beam CT imaging system as provided herein results from recent advances in deformable registration techniques which allow the fusion of two three-dimensional medical images from different modalities, such as Position Emission Tomography (PET)/CT. It is apparent this system offers the ability to fuse three-dimensional data sets from contrast MRI exams with a cone beam CT breast imaging system that provides anatomic landmarks as well as integrated biopsy capability. In this way, an accurate method of biopsy may be carried out in a breast center while the MRI examination may have been conducted at a different location. Following registration of the three-dimensional data sets which may be executed by the processors of the cone beam CT imaging system, a biopsy device may target the MRI enhancement that has been registered and fused with the three-dimensional CT data set. This task is made easier as both imaging systems image the patient in the prone position without compression and accurate registration of the images may be carried out potentially without the use of fiducial markers either on the skin or in the breast tissue.

Following breast conserving surgical treatment (e.g., lumpectomy) of a diagnosed breast cancer, adjuvant radiation is generally used to lower the risk of local cancer recurrence. Accelerated Partial Breast Irradiation (APBI) has recently been gaining favor as it can be delivered in fractions in a week or less compared to conventional radiation therapy which requires six weeks of fractionated radiation. In these types of procedures, brachytherapy or electronic brachytherapy is delivered through a balloon catheter that is generally placed in the lumpectomy cavity by the breast surgeon. A cone beam CT imaging system as described herein may provide an accurate three-dimensional image of the pendulant breast to be treated. This allows for precise measurements of the cavity and the location of the cavity in relation to the skin, areola complex and chest wall of the patient as well as the conformance of the balloon to the lumpectomy cavity.

Radiation treatment planning is currently performed following imaging by conventional MDCT which again subjects the patient to radiation of the heart and lungs. A breast cone beam CT system as described herein may offer the capability of actually using the breast CT system to perform the brachytherapy treatments and on-board imaging may be used to verify the precise location of the balloon in the breast since the formation of a seroma in the lumpectomy cavity may alter the radiation actually delivered to the wall of the lumpectomy cavity.

There has also been interest in delivering an accelerated intensity modulated dose of radiation to the breast using a conventional linear accelerator with the patient in the prone position. See, e.g., Fromenti SG, "*Phase I-II Trial of Prone Accelerated Intensity Modulated Radiation Therapy to the Breast to Optimally Spare Normal Tissue,*" *Journal of Clinical Oncology*, Volume 25(16) at 2236-42, (Jun. 1, 2007). In this type of treatment the patient is treated in a prone position with the breast pendulant. Within the limits of the current design of linear accelerator systems, this type of patient positioning will reduce the amount of radiation to the heart and lung thus providing a potential to reduce cardiac toxicity and fibrosis in the lungs. It is expected that prone breast radiation treatment systems will be developed to totally avoid treating non-target areas such as the thorax. In these types of systems a three-dimensional conformal treatment plan will provide an opportunity to accurately simulate the breast in the prone treatment position and will be enabled by the breast CT system described herein.

A prone breast imaging system as described herein may also provide for image guided surgery of breast cancer. Image guided surgery is routinely used in brain and spinal surgery. These systems provide a three-dimensional preoperative CT or MRI data set that is used to guide surgery where the surgical instruments are encoded with various types of sensors which enable the surgeon to visualize the location of the instrument within the framework of the virtual three-dimensional data set, even though the instrument is not visible under the surgical microscope. There would be substantial benefits to use such an approach to breast surgery but to date all breast surgery is performed with the patient in the supine position, while breast MRI is performed in the prone position. Given soft tissue deformation and the lack of a method to confine the breast in a stable position, image guided surgery of the breast has been limited to the use of ultrasound in the operating room as part of the lumpectomy procedure to aid the surgeon in insuring the cancerous mass is removed. The surgeon does not have correlated or registered image data showing the extent of disease as determined by pre-operative contrast MRI or CT exams.

The prone breast imaging system described herein offers the opportunity to change the paradigm of breast lumpectomy procedures by enabling a method where the surgeon may operate on the patient's breast in the prone position while using the imaging system in surgery as the operating platform. In this type of configuration the three-dimensional cone beam CT data provides a three-dimensional operative field for the surgeon to appreciate the extent of the cancer. Any one of several surgical or ablative methods may be used to remove the cancerous tissue while the ability to conduct intraoperative CT examinations offer the surgeon a new method of determining surgical margins. These types of surgical instruments may be operated within the framework of the guidance device for accurate targeting within the breast so that specific lumpectomy instruments may be used to remove the tissue. Alternatively, surgical instruments may be located in three-dimensional space as is commonly the case in neurosurgical procedures, or current resection devices or electrocautery surgical instruments as used for lumpectomy may be used as they are normally used for the removal and cauterization of breast tissue. The major benefit of such a system is the potential to improve the surgical margins that currently create a major drawback to lumpectomy techniques. Poor surgical margins result in a reoperation range currently from about 10-40%. Improving margin control while achieving good cosmesis is the objective of the surgeon. Gross disease is frequently left in the breast and many times not known since the pathologist only samples the tissue and does not review margins at all contiguous points on the resected tumor.

The system described herein may also allow for the insertion of a brachytherapy balloon at the end of the lumpectomy with immediate delivery of one fraction of radiation to the lumpectomy cavity, particularly in the case of electronic brachytherapy. Research has suggested that one dose of brachytherapy radiation could deliver sufficient dose intraoperatively to the lumpectomy site so that the patient does not need to return for further adjunctive radiation treatment.

In another aspect, a method for computed tomography breast imaging is provided and includes locating a patient's breast within a predetermined frame of reference having a predetermined axis extending away from a boundary plane of the predetermined frame of axis, wherein an axis of the patient's breast extending from the chest wall of the patient to a nipple of the patient's breast is aligned with the predetermined axis (e.g., positioned parallel to or coaxial with the predetermined axis) for imaging. In turn, the method provides for the transmission of an imaging beam from an imaging beam source through the patient's breast, and reception of at least a portion of the imaging beam transmitted through the patient's breast at an imaging signal detector to yield an output signal.

In conjunction with such method, one or both of the imaging beam source an imaging signal detector may be moved relative to the predetermined frame of reference, wherein the output signal comprises projection image data corresponding with a predetermined angular range of projection views of the patient's breast. In turn, computed tomography (CT) processing of the projection image data may provide at least one reconstructed image.

In some embodiments the imaging signal detector may comprise a slot scan detector that includes an array of detector elements, wherein the receiving step may include scanning an active array of the array of detector elements across the patient's breast. In this regard, the active array may have a length defined by at least one column of line detector elements extending parallel to the predetermined axis of the predetermined frame of reference, and having a width defined by at least one detector element extending in a direction orthogonal to the length, wherein the width of the active array is less than a width of a patient breast located within the predetermined frame of reference.

In one approach, an array of detector elements may be moveable relative to the predetermined frame of reference. In turn, the scanning step may comprise moving the array of detector elements relative to the predetermined frame of reference. For example, such scanning may be carried out in timed relation to movement of the imaging beam across a patient's breast.

Alternatively and/or additionally, the array of detector elements may comprise a plurality of columns of aligned detector elements. In turn, the scanning step may comprise activating different ones of the columns to dynamically define the active array of detector elements.

In a further aspect, the locating step may comprise supporting a patient in a prone position on a table, wherein a patient breast is pendulantly received through an aperture of the table to extend into the predetermined frame of reference. In such arrangement, the imaging predetermined frame of reference is located below the patient support table.

In an additional aspect, the transmitting step of the described method may be completed free from passage of the imaging beam through the boundary plane of a predetermined frame of reference, thereby limiting patient exposure to the imaging beam. In this regard, the imaging beam may be transmitted so as to extend parallel to or otherwise diverge away from the boundary plane. Alternatively and or additionally, a radio opaque barrier may be positioned to preclude the passage of the imaging beam across the boundary plane. By way of example, where a patent support table is employed, a radio opaque material may comprise the table.

In a further aspect, the imaging beam employed in the noted method may comprise a divergent beam, wherein the transmitting step comprises moving the divergent beam across the patient's breast in a direction substantially parallel to a chest wall from the patient. By way of example, the divergent beam may comprise a cone beam or a fan-shaped beam. In the later regard, the fan-shaped beam may be provided by blocking portions of a cone-beam generated by an x-ray source.

In certain embodiments, the imaging beam source may be supported by a first support member and the imaging signal detector may be supported by a second support member. In turn, the moving step may comprise pivoting one and/or both of the first support member and the second support member about the predetermined axis of the predetermined frame of reference.

In an additional aspect, the noted method may further comprise introducing an image contrast media into the patient (e.g., iodixanal). For example, the contrast media may be introduced via a vascular catheter.

Relatedly, the processing step may include processing a first portion of the projection image data obtained prior to the introducing step, and processing a second portion of the projection image data obtained after the introducing step, wherein corresponding first and second reconstructed images may be obtained. In turn, the first and second reconstructed images may be utilized (e.g., in an image subtraction sub-step) to generate a contrast-enhanced image. The method may further provide for the display of one or more reconstructed images, or a contrast-enhanced image, on a display.

In yet another aspect, an inventive method may comprise the locating, transmitting, receiving and moving steps noted above, wherein the output signal comprises image data corresponding with at least two views of the patient's breast. In turn, either or both computed tomography processing or stereotactic image generation can be utilized to provide an image (e.g., a two-dimensional image or three-dimensional image). In turn, the method may further include utilizing image data corresponding with a given projection view of the patient's breast to generate fluoroscopic images in quasi real-time. In one approach, the method may further include displaying the quasi real-time fluoroscopic images on a display located adjacent to the predetermined imaging frame of reference. In this regard, such display may be viewed by medical personnel in conjunction with procedures carried out on a patient's breast on a quasi real-time viewing basis. By way of primary example, the display may be viewed by medical personnel carrying out a biopsy procedure (e.g., utilizing a biopsy needle instrument), a surgical procedure (e.g., lumpectomy), and/or a treatment procedure (e.g., brachytherapy).

Additional aspects and advantages of the present invention will become apparent to one skilled in the art upon consideration of the further description that follows. It should be understood that the detailed description and specific examples are intended for purposes of illustration only and are not intended to limit the scope of the invention.

BRIEF DESCRIPTION OF THE DRAWINGS

For a more complete understanding of the present invention and further advantages thereof, reference is now made to the following Detailed Description of the Invention taken in conjunction with the accompanying drawings, wherein.

DETAILED DESCRIPTION OF THE INVENTION

In the following description, the invention is set forth in the context of prone breast imaging and biopsy systems and methods. Certain aspects of the invention may also be employed in upright breast imaging and biopsy systems and methods.

Figure 1:
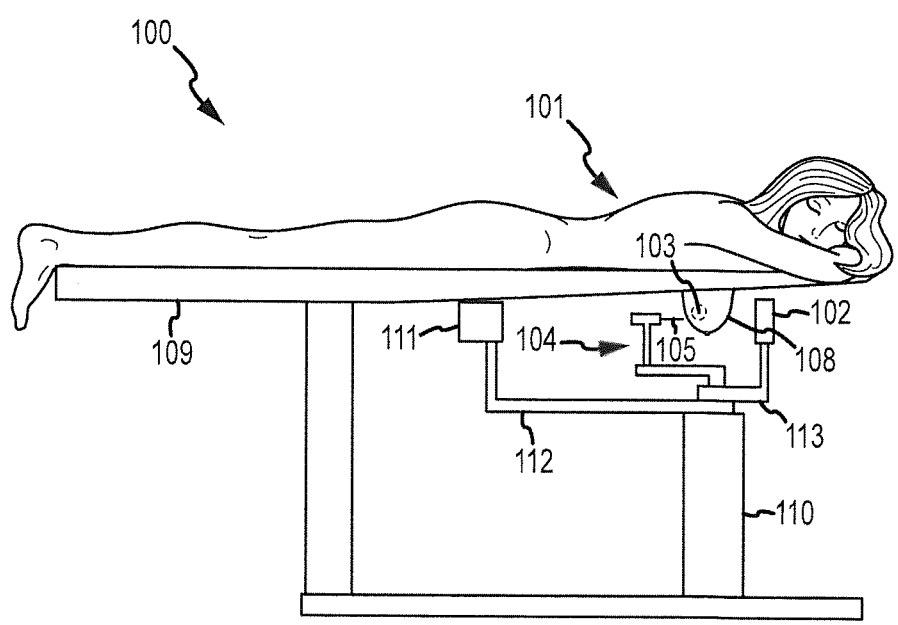
FIG. 1 is a side view illustration of an embodiment of a prone breast imaging and biopsy system and a patient.

FIG. 1 is an illustration of an embodiment of a prone breast imaging and biopsy system 100 and a patient 101. The prone breast imaging and biopsy system 100 includes a detector assembly 102 (e.g., a slot scan detector assembly). The detector assembly 102 may, for example, have an imaging capability of 25 microns. The detector assembly 102 may be positioned behind the area of interest 103 within a breast 108 and may scan rapidly (e.g., from left to right) in order to provide a quasi real time fluoroscopic image of the breast or a region of interest of the breast. The prone CT breast imaging and biopsy system 100 may also include a needle biopsy assembly 104. As a needle 105 is positioned into the area to be biopsied, a fluoroscopic image may provide the ability to direct the needle 105 into the area of interest 103 (e.g., along a path and/or to a desired depth or position), and to confirm the position of the needle 105 relative to the suspicious lesion to be biopsied.

The imaging detector 102 may be positioned to create a stereotactic pair of images of the breast 108 or a CT image of the breast 108 reconstructed from a series of projection views. The needle biopsy assembly 104 may have software that is able to calculate the appropriate trajectory for the needle 105 to be positioned in the area of interest 103 in order to carry out a needle biopsy procedure.

The present invention allows a woman (e.g., patient 101) in a prone position to undergo a high-resolution digital x-ray imaging exam (e.g., 25 micron pixels allows spatial resolution as high as 20 lp/mm) of the entire breast 108. In addition, any part of the breast 108 that may require needle biopsy due to the detected presence of a suspicious lesion may be accessed by an orbital biopsy system, wherein the lesion to be biopsied is positioned at the isocenter of the system such that any entry point on the surface of the breast 108 is available and will ensure that the lesion is sampled when the device tip is advanced into the isocenter of the system which supports the biopsy instrument (e.g., needle 105).

The prone breast imaging and biopsy system 100 may comprise a table 109 with one or two holes for both breasts or one breast and a patient's arm. The breast 108 is pendulant and may be restrained by a compression device (not shown) that facilitates needle biopsy and/or digital mammography. Alternatively, if a three-dimensional image of the breast 108 is desired, the breast 108 may be fixed in a radiolucent holder (not shown) in order to prevent motion during image acquisition as well as to enable biopsy of the breast in a constrained position.

Figure 2:
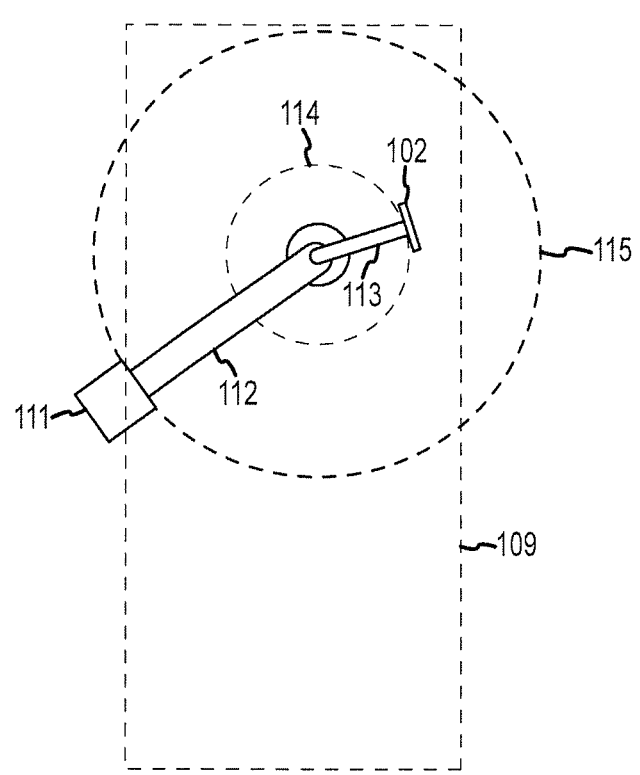
FIG. 2 is a top view schematic diagram of the prone breast imaging and biopsy system of FIG. 1.

FIG. 2 is schematic diagram of the prone breast imaging and biopsy system 100 as seen from above. The table 109 is shown in the phantom dashed lines in FIG. 2. An embodiment may include the table 109 with two concentric support arms 112, 113 that are independent of each other and supported by the pedestal 110 from below the table 109. Means are provided to attach an x-ray source 111 or multiple x-ray sources on the outer ring arm 112. The x-ray source(s) on the outer ring arm 112 may be moved along an encoded arc 115 such that precise location of the corresponding x-ray focal spot(s) is known at all times. The inner ring arm 113 supports a high-resolution detector (one-dimensional or two-dimensional) assembly 102 capable of receiving x-ray signals during a scanning procedure. The x-ray detector 102 is also position encoded so that its precise location along arc 114 is known at all times. Both the inner ring arm 113 and outer ring arm 102 provide means for a motor control of the x-ray source 111 or sources as well as the detector 114. Means is provided for the table 109 to move up and down by a motor and in the x and y planes by bearings supporting the table 109. The two concentric arms 112, 113 provide for clearance for the needle biopsy assembly 104. In this regard, the needle biopsy assembly 104 may be operable to position and advance the needle 105 into the breast 108 at any appropriate angle.

In one preferred method, the outer ring arm 112 provides means for vertical travel to move the focal spot or focal spots in a range at least as long as the maximum length of the detector. The x-ray source(s) 111 may be moved under control of a computer which also activates x-ray energy in a continuous or pulsed mode while a collimator with variable filters may shape the x-ray beam during x-ray exposure. The inner ring arm 113 may also provide means to change the vertical position of the detector assembly 102 at any time during the procedure. The x-ray source 111 and/or the detector assembly 102 may be operable to be swiveled relative to their respective frames 112, 113 and/or tilted. The design provides for totally independent paths of the x-ray focal spot(s) and the x-ray detector assembly 102, unlike currently known cone beam CT breast imaging systems.

Although shown as inner ring arm 113 and outer ring arm 102, other configurations to position the x-ray source 111 or sources and detector 102 or detectors may be utilized. For example, the x-ray source 111 may be interconnected to a C-arm and may be supported and controlled similarly to a conventional C-arm system, albeit placed on its side instead of supported substantially vertically. For another example, the x-ray source 111 may be interconnected to a continuous ring and be supported and controlled similarly to a conventional closed CT x-ray imaging system, albeit placed on its side instead of supported substantially vertically. The detector 102 or detectors may be similarly supported as the x-ray source(s) 111, or may be supported in any of the above-described manners.

In an embodiment, the x-ray source(s) 111 may be independent from the x-ray detector assembly 102. With independent motion control of both the x-ray source 111 and detector assembly 102, which are not configured in a classical rigid frame, it is possible to acquire views that allow the use of both 3rd and 4th generation CT geometries.

The x-ray source 111 may consist of multiple selected x-ray sources or a field emission x-ray source such as described in U.S. Pat. No. 7,227,924 B2 to Zhou et al. These multiple x-ray sources are capable of each pulsing at various temporal frequencies and at varying kVps as well as focal spot sizes and amperage depending on the photon flux requirements as described in U.S. Pat. No. 7,245,692 to Lu et al. This type of configuration allows a unique means of overall system control. Through the recent availability of flexible reconstruction algorithms embodying limited angle and limited view imaging, the x-ray imaging parameters can be modulated during the actual imaging process to optimize image quality, acquisition time, and radiation dose consistent with the area of interest of concern in the breast and the overall purpose of the exam.

The prone CT breast imaging and biopsy system 100 may employ dual energy or polychromatic x-ray imaging. Dual energy x-ray imaging has shown a benefit in imaging tissue by the ability to emphasize characteristics that are visualized easier with higher or lower kV energies. For example, in the case of imaging the breast with non-ionic contrast medium, it is of benefit to image at energies below and above the k-edge of iodine. Acquiring images of the breast at below 30 kVP and above 40 kVP following intravenous injection of contrast media which has its k-edge at 33.16 KeV provides the opportunity to subtract the two images and display the result which will show the contrast distribution with fewer artifacts and allow a more precise diagnosis of the extent of cancer in the breast.

The prone CT breast imaging and biopsy system 100 may include a novel method of determining the x-ray source 111 and/or detector assembly 102 imaging path prior to and during an imaging exam (e.g., CT imaging) of the breast 108. Most CT x-ray imaging systems operate based on a predetermined x-ray imaging protocol and image reconstruction follows after projection images are acquired. The prone breast imaging and biopsy system 100 may allow the area of the breast 108 to be indicated prior to initiation of data acquisition. Based on the requirements of the exam, the number of x-ray exposures required from specific angles or views may be determined such that x-ray exposure is minimized while high-resolution images are reconstructed following the completion of the acquisition sequence. In addition, while data acquisition is underway, information that has been reconstructed may be used to alter the balance of the imaging acquisition protocol in order to insure an optimum result.

Additional image reconstruction capability of the prone CT breast imaging and biopsy system 100 may be enhanced by the use of new algorithms where a limited number of views, and limited angles, can be utilized to reconstruct image data thus delivering a reduced dose of x-ray to the patient. An example of these new algorithms can be found in Emil Y. Sidky et al.; Accurate image reconstruction from few-views and limited-angle data in divergent-beam CT; The Journal of X-Ray Science and Technology; 14:119-139, 2006. As noted, other employable algorithms are disclosed in PCT Publication No. WO2007/095312.

Another benefit of the prone breast imaging and biopsy system 100 incorporating multiple x-ray sources 111 may be that a large number of x-ray views of an object can be acquired with very high temporal resolution since it may not be necessary to physically move the x-ray sources 111. Significant leverage in rapidly acquiring a large number of x-ray views with this type of x-ray source 111 arrangement is provided by embodiments described herein where the x-ray detector 102 is able to move independently of the x-ray source 111 position.

The detector assembly 102 may use a wireless means of transmitting data to a receiver and power may be supplied to the detector 102 by means of an on board battery, or conventional slip ring or radio frequency air coupling technology for providing the electrical power required to activate the detector 102 during a scan. The x-ray source 111 or sources may receive power from conventional high voltage cables or from slip ring technology used routinely in conventional CT scanners.

Figure 3:
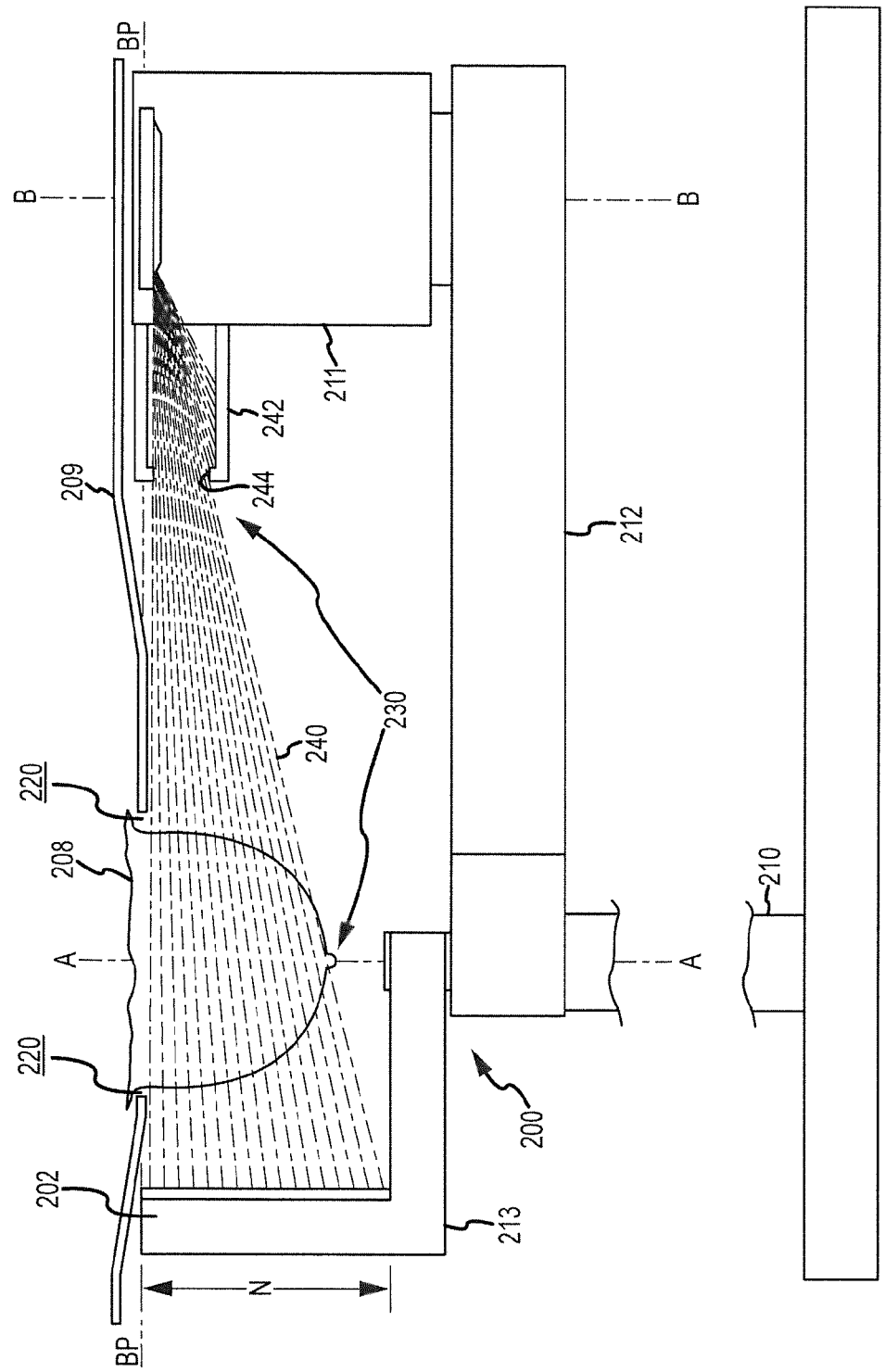
FIG. 3 is a side view illustration of another embodiment of a prone breast imaging system.
Figure 4:
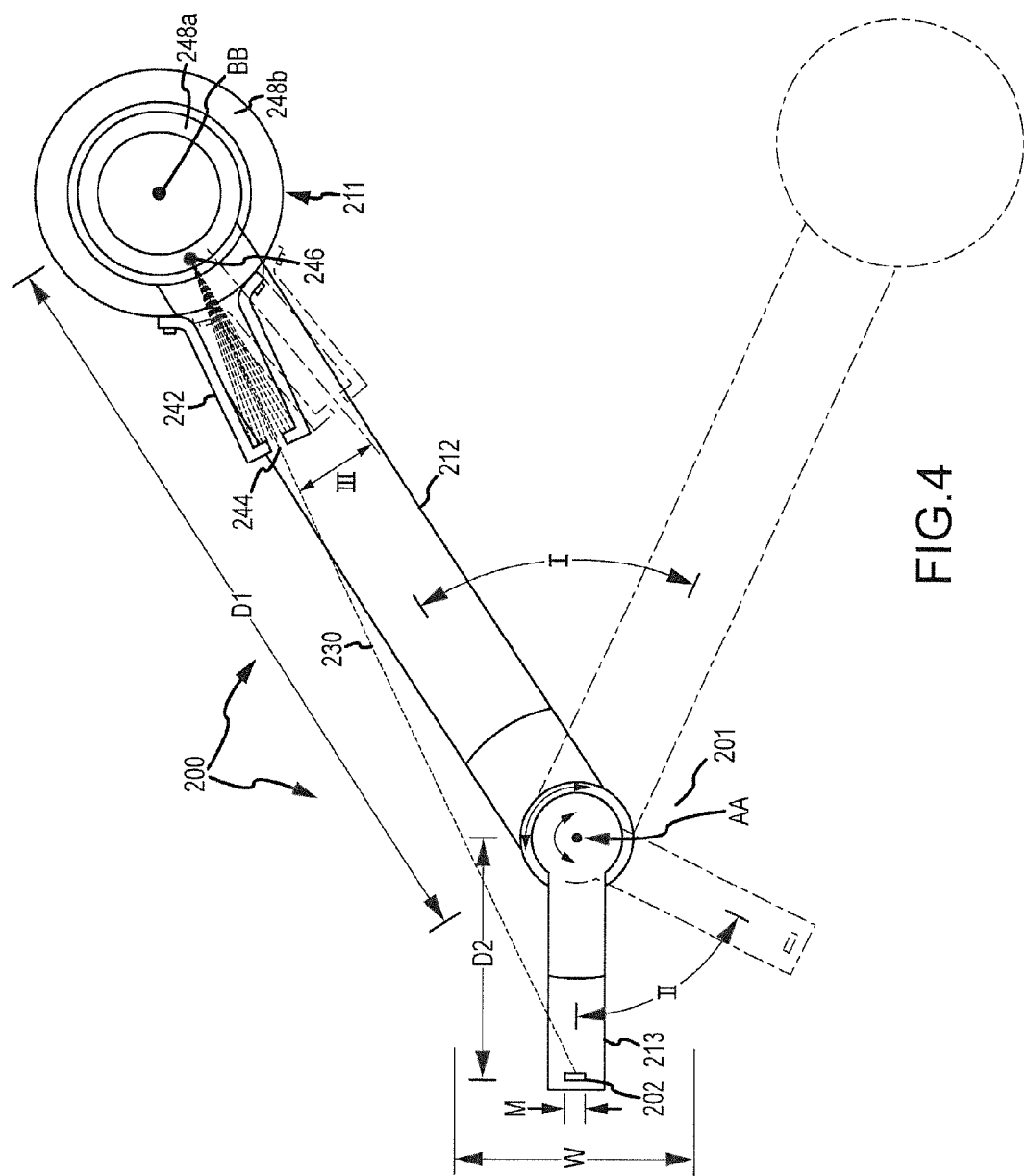
FIG. 4 is a top view illustration of the embodiment of FIG. 3.

Reference is now made to FIGS. 3 and 4 which illustrate another embodiment of a prone CT breast imaging system 200 and a patient breast 208 positioned relative thereto. The prone CT breast imaging system 200 includes an imaging beam source 211 and an imaging detector 202 which are disposed in known relation to define a predetermined imaging frame of reference therebetween. In this regard, the imaging beam source 211 and/or imaging detector 202 may be selectively positioned across a predetermined range of positions, wherein at least a portion of an imaging beam 240 transmitted through the predetermined frame of reference by the imaging beam source 211 may be received by the imaging detector 202 to yield an output signal comprising one-dimensional or two-dimensional image data that corresponds with a plurality of different projection views of a patient breast 208 located in the predetermined frame of reference.

More particularly, the prone breast imaging system 200 may include a patient support table 209 having an aperture 220 for receiving a pendulant patient breast 208 therethrough, wherein the pendulant breast extends into the predetermined frame of reference 230 located bellow the patient support table 209. In turn, the imaging beam source 211 and imaging detector 202 may be disposed for relative movement below the table 209.

In this regard, and as shown in FIG. 3, the imaging beam 240 may be provided so that the rays of the corresponding beam extend parallel to or diverge away from an imaging boundary plane BP. Alternatively, or additionally, a boundary plane BP may be defined by a radio opaque, bottom surface of the patient support table 209 or a similar structure. In either approach, it is desirable to provide an arrangement in which an imaging beam 240 only passes through a patient's breast(s) on a first side of a bounding plane BP and is blocked or otherwise shaped/located to avoid passage through other bodily portions of a patient located on an opposing, second side of a bounding plane BP (e.g., a patient's chest wall or other torso regions).

In the illustrated embodiment, relative movement of the imaging beam source 211 and imaging detector 202 may be realized by supportably mounting the imaging beam source 211 to a first support member 212 that is pivotable about an axis AA extending though the predetermined frame of reference 230. As such, imaging beam source 211 may be moved along an arcuate path, e.g., radially about axis AA, at a first radial distance D1. Further, the imaging beam source 211 may be rotatably mounted to the first support member 212, wherein the imaging beam source 211 is rotatable about an axis BB that may be disposed substantially parallel to axis AA.

Additionally or alternatively in other embodiments, the imaging detector 202 may be supportably mounted to a moveable second support member 213. For example, the second support member 213 may be disposed for pivotable movement about axis AA. As such, imaging detector 208 may be moved along an arcuate path, e.g., radially about axis AA, at a second radial distance D2. In the illustrated embodiment, the first support arm 212 and second support arm 213 may be disposed to extend laterally (e.g., horizontally) from and be supported by an upright (e.g., vertical) pedestal member 210. As further illustrated, radial distance D1 may be greater than radial distance D2 (i.e., D1>D2).

As shown in FIGS. 3 and 4, the aperture 220 may be located so that a pendulant breast 208 positioned therethrough may define a breast axis extending from a patient's chest wall (e.g., orthogonally) through a nipple of the breast 208 alignable with the axis AA noted above. For example, the aperture 220 may be located so that the breast axis is coaxial or otherwise parallel with the axis AA. In the embodiment shown in FIG. 4, the breast axis is coaxial with axis AA.

As illustrated by FIG. 3, the imaging beam 240 may comprise a divergent beam. For example, in the illustrated embodiment, the imaging signal 240 is a fan-shaped beam. The fan-shaped imaging beam 240 may be provided in the illustrated embodiment by an x-ray source 211 that transmits a cone-beam into an interconnected beam shaping member 242 having a slot 244 that defines the fan configuration of the imaging beam 240 by blocking portions of the cone-beam that do not pass through the slot 244. The x-ray imaging source 211 may be provided so that a focal spot 246 of the imaging beam 240 is located on an anode track 248a that is co-rotational with an x-ray tube 248b of the source 211. In another arrangement, an imaging beam source 211 may be fixedly mounted to a first support member 212, and a beam shaping member 242 having a slot 244 may be rotatably mounted to the first support member 212 or imaging beam source 211 to rotate about a focal spot of the imaging beam source 211, wherein an imaging beam may be scanned across a patient's breast in timed relation to slot scanning operation of a slot-scan type imaging-detector (e.g., wherein the imaging beam and active array of the detector are maintained in alignment).

As noted, first support member 212 and second support member 213 may be pivotable about axis AA, and imaging beam source 211 may be rotatable about axis BB. Such relative component moveability allows for the selective obtainment of a range of projection views of a patient breast, while also facilitating the establishment of corresponding limited ranges of componentry movement, e.g., less than 180° relative to pivot axis AA or rotational axis BB, so as to simplify apparatus and operation complexity.

For example, and with particular reference to FIG. 4, the first support member 212 is shown by solid lines in a first position and by phantom lines in a second position, wherein the first support member 212 and imaging beam source 211 may be selectively positioned across an angular range I relative to the axis AA. Similarly, the second support member 213 is shown by solid lines in a first position and by phantom lines in a second position, wherein the second support member 213 and imaging detector may be selectively positioned across an angular range II relative to the axis AA. Further, imaging beam source 211 is shown in solid lines in a first position and in phantom lines in a second position, wherein the imaging beam source 211 and slotted beam shaping member 242 may be selectively positioned across a rotational range III relative to axis BB.

In one implementation angular range I may be established at equal to or less than 270°, angular range II may be established at equal to or less than 270° and angular range III may be established at equal to or less than 180°. In another implementation, angular range 1 may be established at equal to or less than 180°, angular range II may be established at equal to or less than 180° and angular range III may be established at equal to or less than 90°. In yet another implementation angular range 1 may be established at equal to or less than 90°, angular range II may be established at equal to or less than 90° and angular range III may be established at equal to or less than 45°. In each of the noted implementations it may be preferred to establish angular range I and angular range II at equal or greater than 30°.

As may be appreciated, the pivotable movement of the first support member 212 and second support member 213, and the rotational movement of the imaging beam source 211, may be automated via a single or multiple drivers. For example, a servo motor(s) may be provided at the pedestal 210 for selective pivotal movement of first support member 212 and second support member 213. Further, a servo motor may be provided at the interface between the imaging beam source 211 and the first support member 212 for selective rotational movement of the imaging beam source 211.

The automated movement of the noted componentry may be timed-coordinated in accordance with one or more predetermined control protocols to obtain the desired projection views of a patient breast. For example, control logic may provide for synchronized relative movement and/or sequential movement of the noted components.

By way of example, in one approach one or more automated drive(s) may be processor controlled so that the first support member 212 moves across a predetermined angular range I over a time period R1 which is greater than a time period R2 over which a second support member 213 moves through a corresponding angular range II. In one implementation R2 may be at least two times greater than R1. As may be appreciated, the processor controlled, automated drive(s) may also be provided to yield different velocity profiles (e.g., non-linear profiles) for the imaging beam source 211 located on the first support member 212 and the imaging detector 202 located on the second support member 213. In conjunction with the noted approach, a computer-controlled drive may also be provided so as to rotate an imaging beam source 211 through a rotational range III over a time period R3 that is substantially the same as the R2 time period for the second support member 213 and image detector 202 mounted thereupon.

In one example, the first support member 212 and supported imaging beam source 211 may be positioned at a plurality of different angular positions relative to axis AA for breast imaging, wherein two or more stereotactic images or a CT image may be generated (e.g., by successively moving the imaging beam 240 (e.g., via rotational movement about axis BB) in timed-relation to radial movement of the second support member 213 and a slot scan detector 202 supported thereby). In turn, a three-dimensional image may be displayed and reviewed by medical personnel. Then, the first support member 212 and imaging beam source 211 may be positioned at a set location for fluoroscopic breast imaging (e.g., by successively moving the imaging beam 240 (e.g., via rotational movement about axis BB) in timed-relation to radial movement of the second support member 213 and a slot scan detector 202 supported thereby). A biopsy, surgical or treatment procedure may be completed during fluoroscopic breast imaging, wherein progressive device positioning may be viewed by medical personnel.

Figure 5:
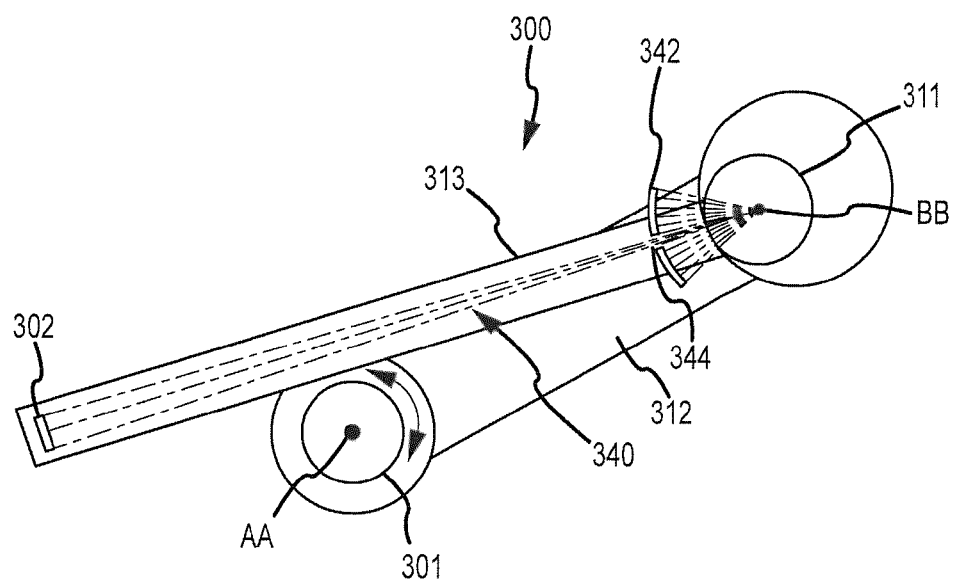
FIG. 5 is a top view illustration of yet another embodiment of a prone breast imaging and biopsy system.

Reference is now made to FIG. 5 which illustrates another embodiment of a prone breast imaging system 300 and a patient breast 301 positioned relative thereto. In this embodiment, an imaging beam source 311 may be supportably mounted to a first support member 312 that is pivotable about an axis AA. Unlike the embodiment shown in FIGS. 3 and 4, the imaging beam 311 may be fixedly mounted to the first support member 312. Further, an imaging detector 202, may be supportably mounted to a second support member 313 that is pivotably mounted to the first support member 312. Relatedly, a beam shaping member 342 having a slot 346 may be fixedly interconnected to the second support member 313 for co-movement therewith.

In this regard, the imaging beam source 311 may be provided to transmit an imaging beam 340 that comprises a cone-beam, wherein the slot 346 of the beam shaping member 344 defines a fan beam configuration for a portion of the imaging beam 340 that is transmitted through the slot 346. It may be appreciated that, by fixedly interconnecting the slotted beam shaping member 344 to the second support member 313, different portions of the cone beam imaging beam 340 transmitted by the imaging source 311 may be utilized to define the fan-shaped beam as the second support member 313 and the imaging detector 312 interconnected thereto are pivoted across a predetermined angular range relative to the first support member 312.

Figure 6:
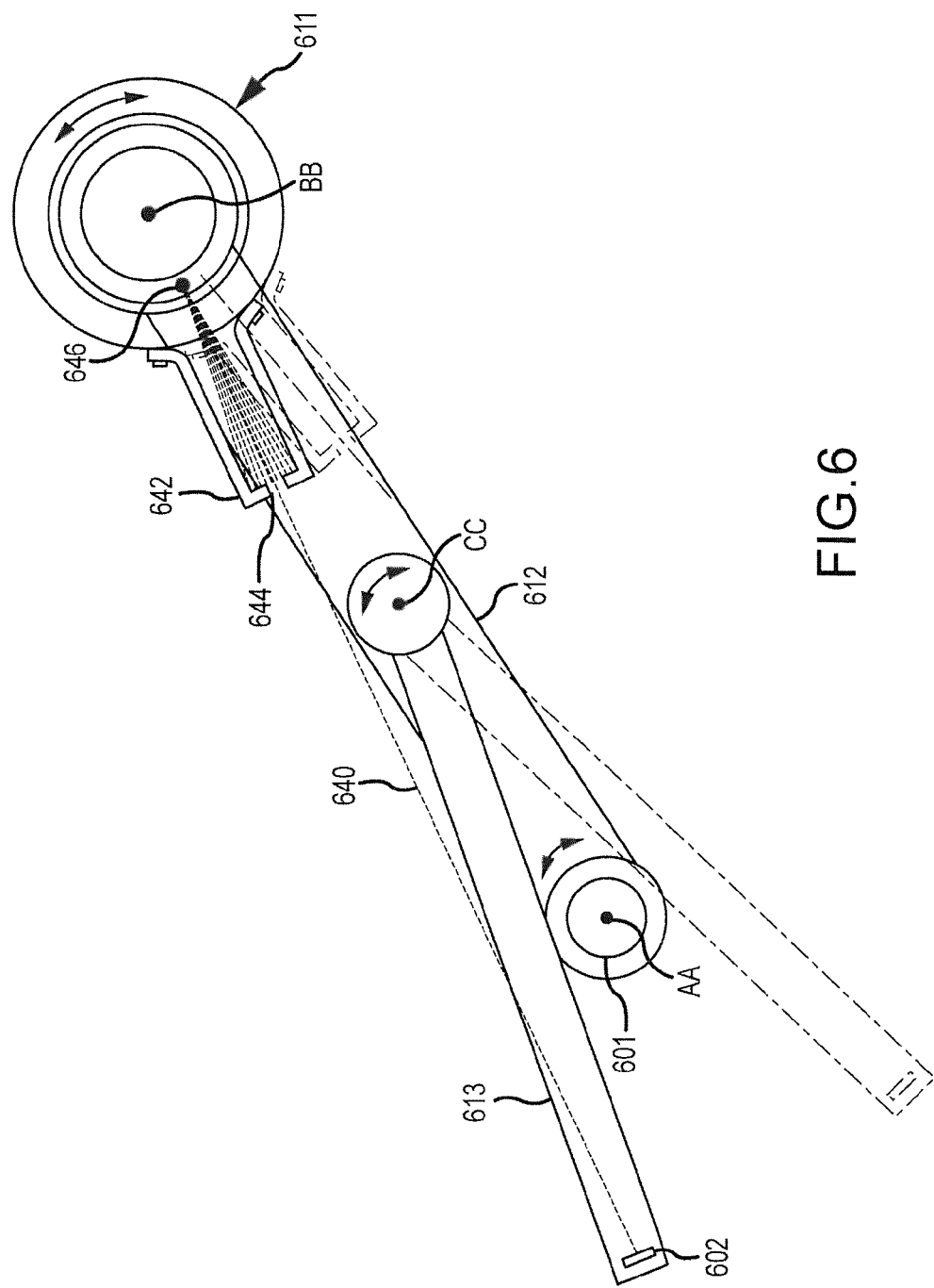
FIG. 6 is a top view illustration of yet another embodiment of a prone breast imaging and biopsy system.

Reference is now made to FIG. 6 which illustrates another embodiment of a prone breast imaging system 600 and a patient breast 601 positioned relative thereto. The prone breast imaging system 600 comprises selected features of the embodiment corresponding with FIGS. 3 and 4, and the embodiment corresponding with FIG. 5. In the former regard, an imaging beam source 611 may be supportably mounted to a first support member 612 that is pivotable about an axis AA. As such, the imaging beam source 611 may be moved along an arcuate path, e.g., radially about axis AA. Further, the imaging beam source 611 may be rotatably mounted to the first support member 612, wherein the imaging beam source 611 is rotatable about an axis BB that may be disposed substantially parallel to axis AA. In turn, a fan-shaped imaging beam 640 may be scanned across a patient breast 601 in a side-to-side direction. In this regard, the imaging beam source 611 may transmit a cone-beam into an interconnected beam shaping member 642 having a slot 644 that defines the fan configuration of the imaging beam 640 by blocking portions of the cone-beam that do not pass through the slot 644. As illustrated, an imaging detector 602 may be supportably mounted to a second support member 613 that is pivotably mounted along the length of first support member 612 for pivotable movement about a pivot axis CC.

Figure 7A:
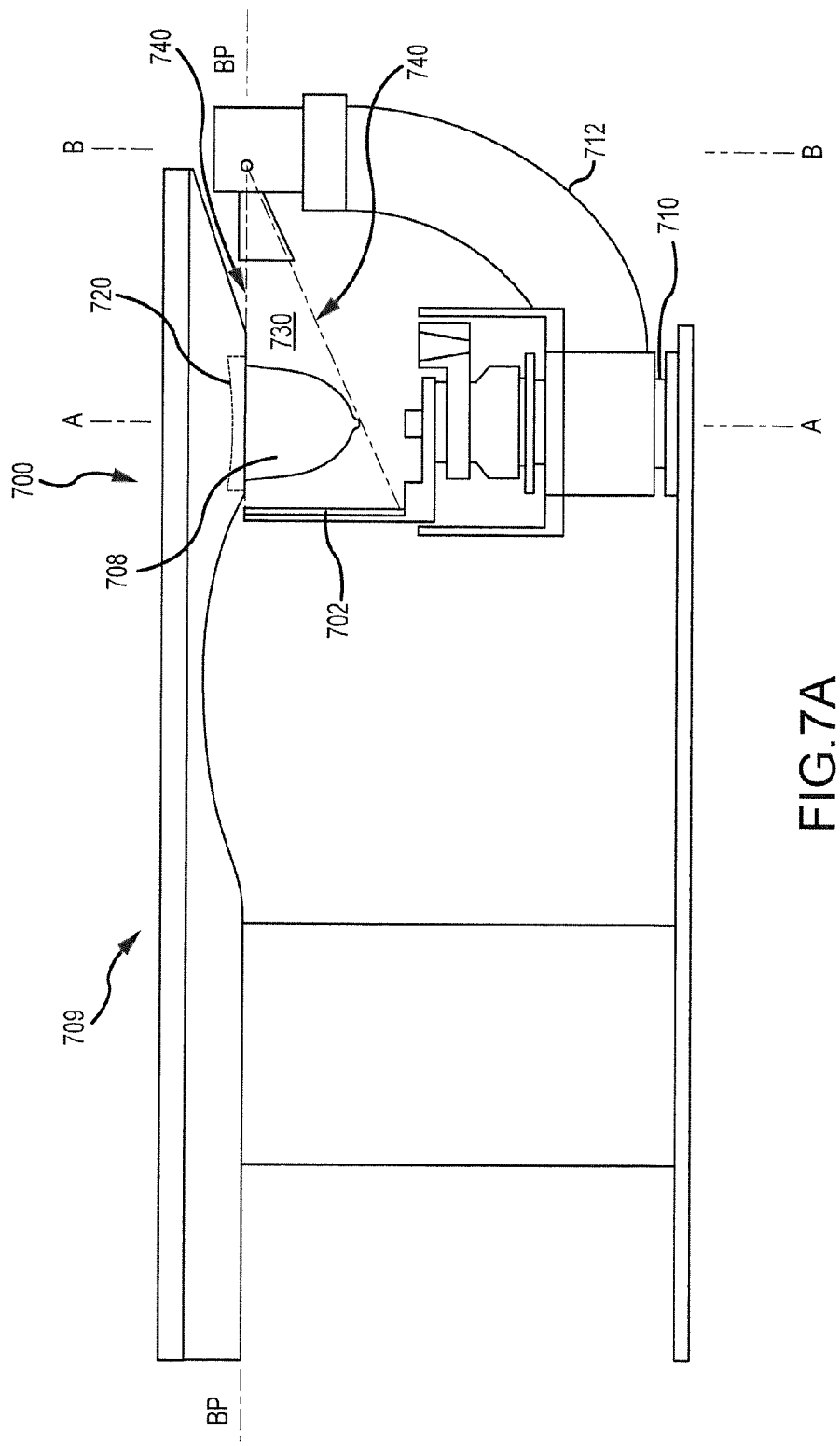
FIG. 7A is a side view illustration of another embodiment of a prone breast imaging system.
Figure 7B:
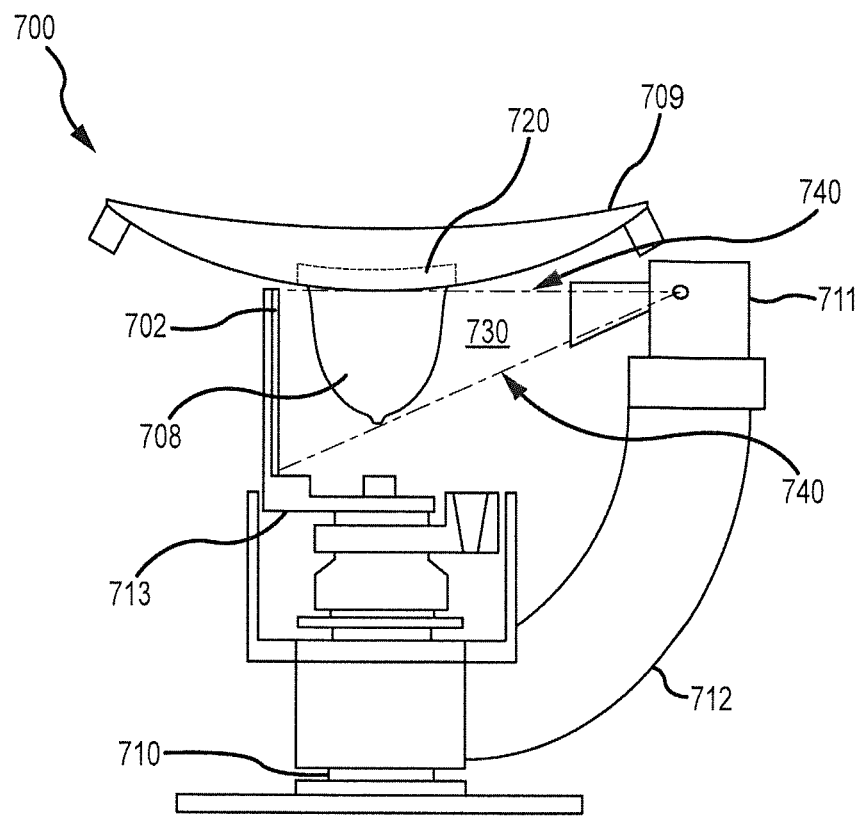
FIG. 7B is an end view of the embodiment of FIG. 7A, with the imaging source and imaging detector of FIG. 7A each rotated 90° from the positions shown in FIG. 7A.
Figure 7C:
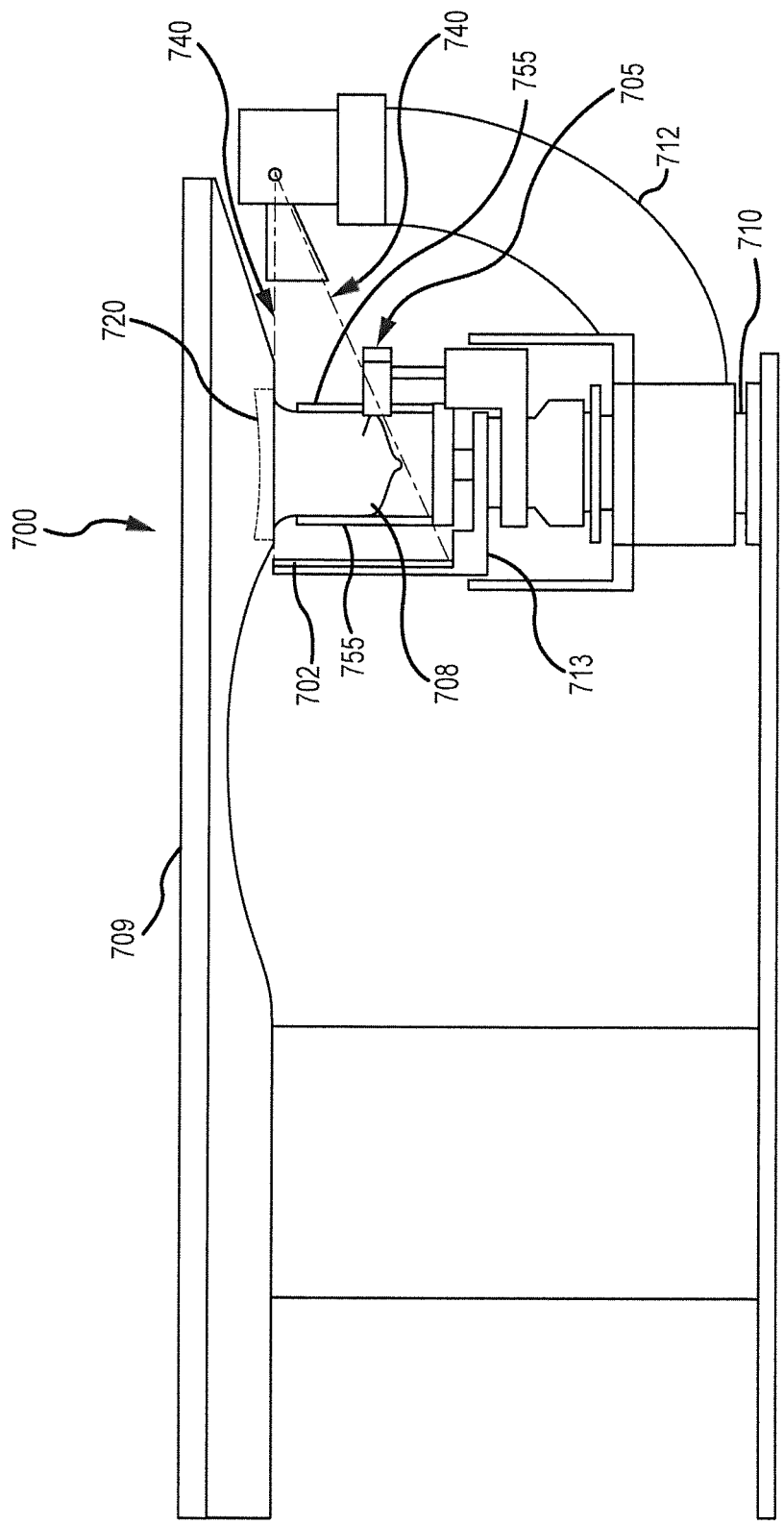
FIG. 7C is another side view illustration of the embodiment of FIG. 7A, with opposing compression plates and a biopsy device interconnected for use.

Reference is now made to FIGS. 7A, 7B, and 7C, which illustrate yet a further embodiment of a prone breast imaging system 700 and a patient breast 701 positioned relative thereto. The prone breast imaging system 700 comprises features similar to the features shown in relation to the embodiment corresponding with FIGS. 1 and 2, and the embodiment corresponding with FIGS. 3 and 4. In this regard, the prone imaging system 700 may include a patient support table 709 having an aperture 720 for (shown in phantom lines) receiving a pendulant patient breast 708 therethrough, wherein the pendulant breast 708 extends into a predetermined frame of reference 730 located below the patient support table 709.

As best shown by FIG. 7B, a portion of a top surface of the patient support table 709 may be contoured to define a concave or recessed region through which aperture 720 is provided. Relatedly, and as best shown by FIG. 7A, a bottom surface of the support table 709 may be contoured define a concave or recessed region sized and located to receive a portion of an imaging beam source 711 and/or imaging detector 702 during imaging operation of the prone breast imaging system 700.

In this regard, the imaging beam source 711 and an imaging detector 702 may be disposed in opposing known relation to define a predetermined imaging frame of reference 730 therebetween, and patient breast 708 may be pendulantly extended into the predetermined frame of reference 730. In turn, the imaging beam source 711 and/or imaging detector 702 may be selectively positioned across a range of imaging positions, wherein a plurality of different projection views of a patient breast 708 may be obtained.

In this regard, an imaging beam signal 740 may be provided by imaging beam source 711 so that the rays of the corresponding beam may extend parallel to an imaging boundary plane BP. Again, as noted above, the boundary plane BP may alternatively be defined by a radio opaque bottom surface of the patient support table 709 or a similar structure. In either approach, imaging beam 740 may be provided that only passes though a patient's breast 708 thereby reducing the source imaging signal dosage.

In this embodiment, relative movement of the imaging beam source 711 and imaging detector 702 may be realized by supportably mounting the imaging beam source 711 to an arcuate support member 712 that is pivotable about an axis AA extending through the predetermined frame of reference 730. In the later regard, the aperture 720 may be disposed so that a pendulant patient breast 708 positioned therethrough may define a breast axis extending from a patient's chest wall (e.g., orthogonally) through a nipple of the breast 708 that is alignable with the axis AA. For example, the aperture 720 may be located so that the breast axis is coaxial or otherwise parallel with axis AA. In the embodiment shown in FIGS. 7A, 7B, and 7C, the breast axis is coaxial with axis AA.

Since the support member 712 is pivotable about axis AA, the imaging beam source 711 may be moved along an arcuate path, e.g., radially about axis AA. Further, the imaging source may be rotatably mounted to the first support member 712, wherein the imaging beam source 711 is rotatable about an axis BB that may be disposed substantially parallel to axis AA.

As shown, the imaging detector 702 may be supportably mounted to a moveable second support member 713. More particularly, the second support member 713 may be disposed for pivotable movement about axis AA. As such, imaging detector 702 may be moved along an arcuate path, e.g., radially about axis AA. In the illustrated embodiment, the first support arm 712 and second support arm set 713 may be disposed to extend laterally (e.g., horizontally) from and be supported by an upright (vertical) pedestal member 710.

As best illustrated by FIG. 7A imaging beam 740 may comprise a divergent beam. For example, the imaging beam 740 may be fan-shaped. The fan-shaped imaging beam 740 may be provided by an x-ray imaging beam source 711 that transmit(s) a cone-beam into an interconnected beam shaping member 742 having a slot that defines the fan configuration by blocking portions of the cone-beam that do not pass through the slot. The x-ray imaging beam source 711 may be provided so that a focal point 746 of the imaging beam 740 is located on an annular track that is a-rotational with an x-ray tube comprising the source 711.

As shown in FIG. 7C, the prone breast imaging system 700 may be configured to further comprise a biopsy, surgical, or treatment instrument 705, and opposing compression plates 755. In this regard, the compression plates 755 may be selectively positioned to immobilize a patient breast 708 for imaging and/or a biopsy, surgical and/or treatment procedure. In biopsy/surgical/treatment procedures, the instrument 705 may be manually and/or automatically positioned so as to selectively remove a tissue sample or to selectively remove or treat a tissue mass from a targeted region. As noted above, quasi real-time imaging utilizing the source 711 and detector 702 may yield images displayable on a user interface (not shown) positioned adjacent to the predetermined frame of reference 730. In turn, the displayed images may be dynamically viewed by medical personnel during a procedure to position and reposition the instrument 705 as desired. In the later regard, instrument 705 may be disposed for pivotal movement about and along axis AA, as well as angular positioning and displacement relative axis AA.

Figure 8:
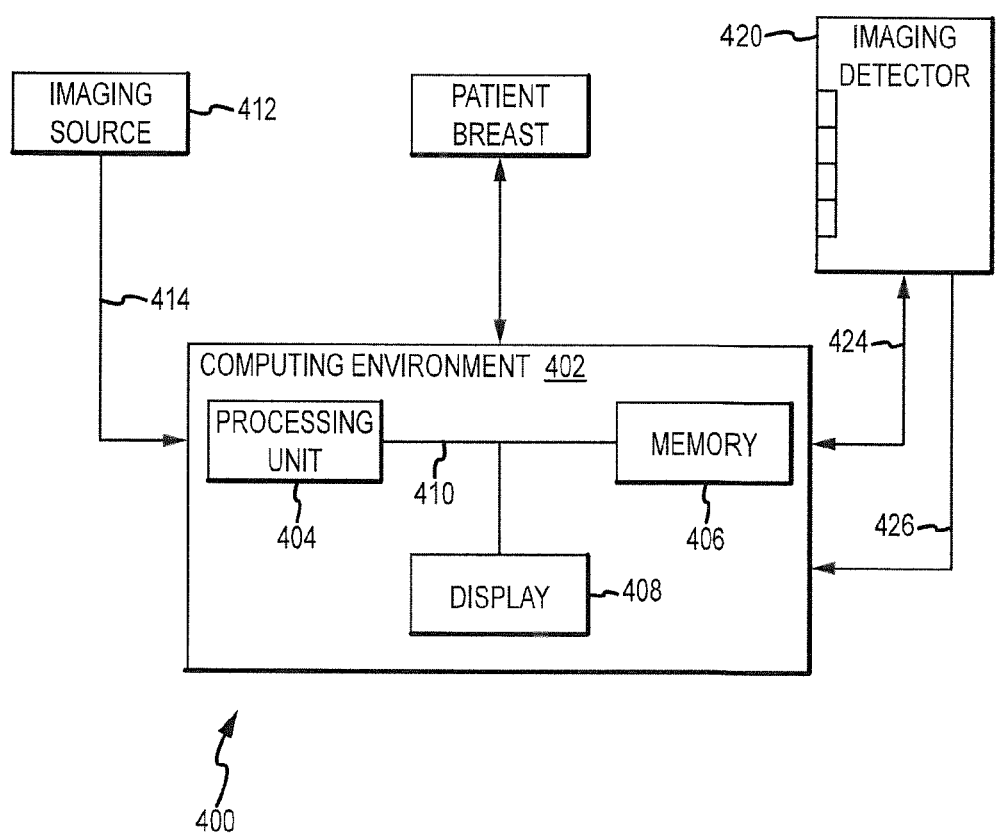
FIG. 8 is a schematic diagram of an exemplary imaging system.

With reference to FIG. 8, an exemplary imaging system 400 for implementing the invention includes a general purpose computing device in the form of a computing environment 402, including a processing unit 404, a system memory 406, and display 408. A system bus 410 may couple various system components of the computing environment 402, including the processing unit 404, the system memory 406, and the display 408. The processing unit 404 may perform arithmetic, logic and/or control operations by accessing system memory 406. For example, the processing unit 404 may control the various system components to acquire data for imaging and may process the acquired data to generate an image. Alternatively, different system processors, or different devices including, for example, graphical processing units (GPUs) may control the various system components to acquire data for imaging and may process the acquired data to generate an image.

The system memory 406 may store information and/or instructions for use in combination with processing unit 404. For example, the system memory 406 may store computer readable instructions, data structures, program modules or the like for operation of the imaging system 400, including, for example, control of movement of any of an imaging source 412, and imaging detector 420 and control of the functionality of the source and the detector, as discussed below. Further, the system memory 406 may store data obtained from detector 420 and the processor 404 or auxiliary processor such as GPUs may process the data for display on the display 408, as discussed in more detail below. The system memory 406 may include volatile and non-volatile memory, such as random access memory (RAM) and read only memory (ROM). It should be appreciated by those skilled in the art that other types of computer readable media which can store data that is accessible by a computer, such as magnetic cassettes, flash memory cards, random access memories, read only memories, and the like, may also be used in the exemplary computer environment. A user may enter commands and/or information, as discussed below, into the computing environment 402 through input devices such as a mouse and keyboard (not shown). The commands and/or information may be used to control operation of the imaging system, including acquisition of data and processing of data.

FIG. 8 further shows imaging source 412 communicating with computing environment 402 via line 414. Source 412 may be stationary or may move relative to and imaging detector 420. Line 414 may also control movement of source 412, such as by sending commands to a motor (not shown) to move all or a part of source 412. For example, in relation to the embodiment of FIGS. 3 and 4 above, the motor may move the imaging source 211 by pivoting a first support member 212 or by rotating the imaging source 211 relative to the first support member 212.

FIG. 8 further shows detector 420 communicating with computing environment 402 via lines 424 and 426. Line 424 may comprise a control line whereby the processing unit may control at least one characteristic of detector 420. Line 426 may comprise a data line whereby a detector output signal comprising image data sensed from the detector may be sent to computing environment 402 for processing by processing unit 404 (e.g., digital image processing). Detector 420 may be stationary or may move relative to source 412. Line 424 may control movement of detector 420, such as by sending commands to a motor (not shown) to move all or a part of detector 420. For example, in relation to the embodiment of FIGS. 3 and 4 above, the motor may move an imaging detector 202 by pivoting a second support member 213.

As noted above, imaging systems comprising the present invention may include an imaging detector that provides an output signal comprising projection image data corresponding with a predetermined angular range of projection views of a patient's breast, and a processor for processing such projection image data to provide an image signal (e.g., via computed tomography processing or utilizing fluoroscopic image generation). In turn, such imaging signal may be utilized to display two dimensional and/or a three dimensional images of a patient's breast to medical personnel. In turn, such images may be utilized for diagnostic purposes, and additionally for use in planning and completing a tissue biopsy procedure. In the later regard, two dimensional and/or three dimensional images may be utilized in connection with the positioning and advancement of a biopsy device relative to a patient's breast.

In conjunction with imaging systems of the present invention, the image data output by an imaging detector may correspond with a 360° angular range of projection views relative to a patient's breast, wherein the data may be processed utilizing conventional computer tomography fan beam or cone beam reconstruction algorithms. Alternatively, and as noted above, relatively new algorithms may be employed to facilitate the use of a limited angular range of projection views, and corresponding image data, in reconstructing image data.

Figure 9:
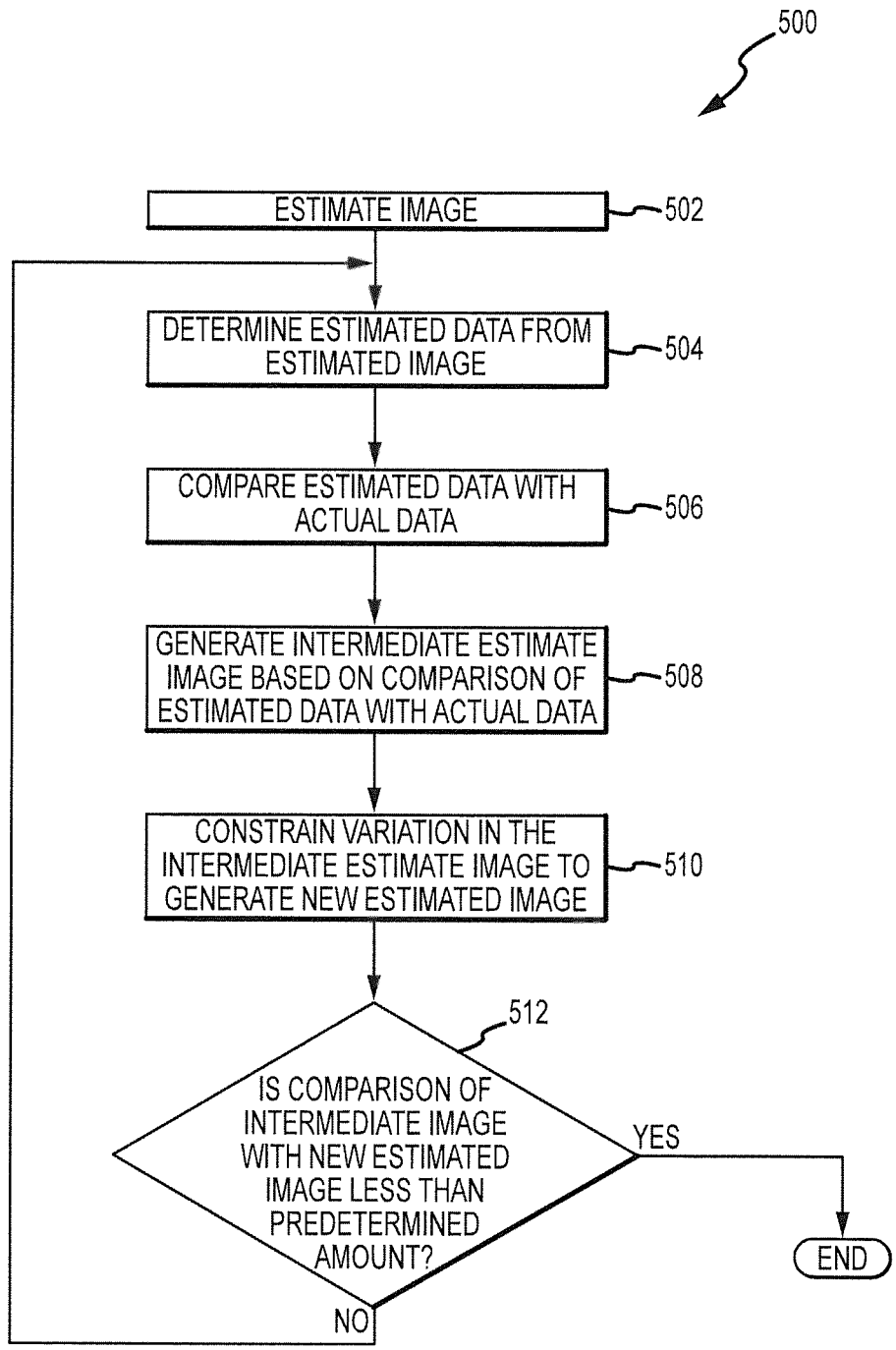
FIG. 9 is a flow diagram of one embodiment of an image reconstruction methodology employable in conjunction with the systems described in FIGS. 1-6.

In this regard, and by way of particular example, image reconstruction methodology and algorithms may be utilized as disclosed in the above-referenced PCT Publication No. WO2007/095312. The basic methodology described in the referenced publication is to iteratively constrain the variation of an estimated image in order to reconstruct an image. In this regard, and with reference to FIG. 9, a flow chart 500 of one example of the methodology is illustrated. As shown at block 502, an initial estimate of the image to be recovered may be selected or generated. The initial estimate may be part of an initialization procedure.

As shown at block 504, using the initial estimate, estimated measurements may be determined. One example of determining the estimated measurements may include using a linear transform operator to determine a linear transform of the initial estimate image.

An intermediate image may be determined based on the estimated measurements. For example, the intermediate image may be determined based on a comparison of the estimated data with the actual data. As shown at blocks 506 and 508, the intermediate image is determined. As shown at block 506, the estimated data is compared with the actual data. One example of comparing the estimated data with the actual data comprises determining the difference. As shown at block 508, the intermediate estimate may be generated based on the comparison of the estimated data with the actual data. For example, the intermediate estimate may be generated using the adjoint, the approximate adjoint, the exact inverse, and/or the approximate inverse of the linear transform operator. Further, the intermediate estimate may be derived from the image or by reducing (in one step or iteratively) the differences between the estimated and actual measurements.

A new estimated image may be determined by analyzing at least one aspect (such as variation) of the intermediate estimate image. Specifically, the variation in the intermediate estimate image may be constrained to generate the new estimated image, as shown at block 510. For example, generalized total variations (TVs) from Sidky et al. of the intermediate estimated image may be minimized to generate the new estimated image. The new estimated image may be used as the initial estimate for block 504 and blocks 504 through 512 may be repeated until the intermediate estimated image and new estimated image converge (such as be less than a predetermined amount, as shown at block 512) or until the estimated data is less than a predetermined amount than the actual data. One may use either intermediate estimated image or the new estimated image as the final estimate of the image. The intermediate image may generally be less smooth than the new estimated image.

Various aspects of the present invention may also be implemented in arrangements where a patient is positioned upright. In such arrangements, a patient's breast may be immobilized between opposing compression plates for imaging and/or biopsy procedures. Relatedly, the features of the embodiment shown in FIGS. 3 and 4 may be translated, or rotated 90°. In relation to all embodiments described herein, a patient's breast may be located in a cup-shaped, radiolucent holder to facilitate biopsy procedures.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A breast imaging apparatus, comprising:
   a locator for positioning a breast of a patient within a predetermined frame of reference having a predetermined axis extending away from a boundary plane of the predetermined frame of reference, wherein an axis of the breast that extends from a chest wall of the patient through a nipple of the breast is alignable with said predetermined axis for imaging;
   a first support member pivotably mounted to a pedestal, wherein the first support member pivots about the predetermined axis;
   an imaging beam source mounted to the first support member for transmitting an imaging beam through said predetermined frame of reference;
   a second support member pivotably mounted to the first support member at an adjoinment location offset from said predetermined axis;
   an imaging signal detector mounted to the second support member for receiving said imaging beam and providing an output signal in response thereto, wherein said imaging beam source and said imaging signal detector are each moveable relative to said predetermined frame of reference and are moveable relative to one another, wherein said output signal comprises projection image data corresponding with a predetermined angular range of projection views of the breast, and wherein said imaging signal detector comprises:
an array of detector elements, comprising an active array of detector elements configured to scan across a region of interest within said predetermined frame of reference, said active array of detector elements having a length defined by at least one column of aligned detector elements extending parallel to said predetermined axis of said predetermined frame of reference and having a width defined by at least one detector element extending in a direction orthogonal to said length, wherein said width of the active array is less than a width of the breast located within said predetermined frame of reference; and,
a processor for computed tomography processing said projection image data to provide a reconstructed image.

2. An apparatus as recited in claim 1, wherein said locator comprises:
a table for supporting the patient in a prone position, wherein said table includes at least one aperture for receiving the breast therethrough.

3. An apparatus as recited in claim 2, wherein said table is selectively, vertically positionable.

4. An apparatus as recited in claim 1, wherein said locator comprises:
a holder for holding the breast in a fixed position within said predetermined frame of reference.

5. An apparatus as recited in claim 4, wherein said holder consists of one of a cup-shaped member for receiving the breast therewithin or a pair of opposing plate members for compressively engaging the breast therebetween.

6. An apparatus as recited in claim 5, further comprising:
a display for utilizing said image signal to display one or more images of the breast located within said predetermined frame of reference.

7. An apparatus as recited in claim 6, further comprising:
a device supportable in known relation to said predetermined frame of reference, wherein said display is located to be viewable by a user when operating said device, wherein said device is selected from a group of a biopsy device, a surgical device and a treatment device.

8. An apparatus as recited in claim 1, wherein said imaging beam source is selectively, radially positionable across a first predetermined angular range relative to said predetermined axis of said predetermined frame of reference.

9. An apparatus as recited in claim 1, wherein said imaging beam source is selectively, radially positionable across a first predetermined angular range relative to said predetermined axis of said predetermined frame of reference, and wherein said imaging signal detector is selectively positionable across a second predetermined angular range relative to said predetermined axis of said predetermined frame of reference.

10. An apparatus as recited in claim 9, wherein said first predetermined angular range and said second predetermined angular range are each 270°.

11. An apparatus as recited in claim 1, wherein said imaging beam source is moveable relative to said first support member.

12. An apparatus as recited in claim 11, wherein said imaging beam source is rotatably positionable across a predetermined rotation range relative to said first support member.

13. An apparatus as recited in claim 12, wherein said predetermined rotation range is 180°.

14. An apparatus as recited in claim 1, further comprising:
at least one automated drive, operatively interconnected to said processor, for automated positioning of said first support member and said second support member to provide a predetermined plurality of projection views within said predetermined angular range.

15. An apparatus as recited in claim 1, wherein said imaging beam source and said imaging signal detector are each moveable relative to said locator.

16. An apparatus as recited in claim 1, wherein said array of detector elements comprises a plurality of columns of aligned detector elements, and wherein different ones of said columns are activated during operation to define said active array of detector elements.

17. A breast imaging apparatus, comprising:
a locator for positioning a breast of a patient within a predetermined frame of reference having a predetermined axis extending away from a boundary plane of the predetermined frame of reference, wherein an axis of the breast that extends from a chest wall of the patient through a nipple of the breast is alignable with said predetermined axis for imaging;
a first support member pivotably mounted to a pedestal, wherein the first support member pivots about the predetermined axis; an imaging beam source mounted to the first support member for transmitting an imaging beam through said predetermined frame of reference;
a second support member pivotably mounted to the first support member at an adjoinment location offset from said predetermined axis;
an imaging signal detector mounted to the second support member for receiving said imaging beam and providing an output signal in response thereto, wherein said imaging beam source and said imaging signal detector are each independently moveable relative to said predetermined frame of reference and are independently moveable relative to one another, and wherein said output signal comprises projection image data corresponding with a predetermined angular range of projection views of the breast; and,
a processor for computed tomography processing said projection image data to provide a reconstructed image, using an estimated image, wherein said computed tomography processing includes iteratively generating the estimated image using said projection image data and constraining variation of the estimated image.

* * * * *